US012766554B2

(12) United States Patent
Jumbe et al.

(10) Patent No.: US 12,766,554 B2
(45) Date of Patent: Oct. 20, 2026

(54) MULTI-LAYERED TRANSDUCER

(71) Applicants: Nelson L. Jumbe, Mountain View, CA (US); Andreas Schuh, Mountain View, CA (US); Peter Rexelius, Mountain View, CA (US); Michael Morimoto, Mountain View, CA (US); Wiljan Smaal, Mountain View, CA (US); Georges Hadziioannou, Mountain View, CA (US); Guillaume Payrot, Mountain View, CA (US)

(72) Inventors: Nelson L. Jumbe, Mountain View, CA (US); Andreas Schuh, Mountain View, CA (US); Peter Rexelius, Mountain View, CA (US); Michael Morimoto, Mountain View, CA (US); Wiljan Smaal, Mountain View, CA (US); Georges Hadziioannou, Mountain View, CA (US); Guillaume Payrot, Mountain View, CA (US)

(73) Assignee: LEVEL 42 AI INC., Mountain View, CA (US)

( * ) Notice: Subject to any disclaimer, the term of this patent is extended or adjusted under 35 U.S.C. 154(b) by 755 days.

(21) Appl. No.: 18/316,596

(22) Filed: May 12, 2023

(65) Prior Publication Data

US 2023/0364643 A1 Nov. 16, 2023

Related U.S. Application Data

(63) Continuation of application No. PCT/US2021/059193, filed on Nov. 12, 2021.
(Continued)

(51) Int. Cl.
*B06B 1/06* (2006.01)
*H10N 30/00* (2023.01)
(Continued)

(52) U.S. Cl.
CPC ......... *B06B 1/0622* (2013.01); *H10N 30/045* (2023.02); *H10N 30/06* (2023.02);
(Continued)

(58) Field of Classification Search
CPC ...... H10N 30/302; H10N 30/308; H04R 1/46; H04R 17/025
See application file for complete search history.

(56) References Cited

U.S. PATENT DOCUMENTS 6,508,747 B1 1/2003 Cook
7,301,687 B2 11/2007 Berggren et al.
(Continued)

FOREIGN PATENT DOCUMENTS

EP 0606767 B1 3/1998
EP 2299574 A2 3/2011

OTHER PUBLICATIONS

International Search Report and Written Opinion issued in corresponding International application No. PCT/US2021/059193 on Apr. 7, 2022.

*Primary Examiner* — Emily P Pham
(74) *Attorney, Agent, or Firm* — BCF LLP

(57) ABSTRACT

There is disclosed a transducer and a method for generating the transducer. The transducer is formed on a substrate layer. The transducer includes a first electrode layer, a first piezoelectric layer on the first electrode layer, and a second electrode layer on the first piezoelectric layer. The first electrode layer is connected to a first electrical connector and the second electrode layer is connected to a second electrical connector. The transducer can be configured to act as an acoustic sensor or an electric potential sensor.

19 Claims, 12 Drawing Sheets

Related U.S. Application Data

(60) Provisional application No. 63/113,094, filed on Nov. 12, 2020.

(51) Int. Cl.

| | |
|---|---|
| ***H10N 30/045*** | (2023.01) |
| ***H10N 30/06*** | (2023.01) |
| ***H10N 30/077*** | (2023.01) |
| ***H10N 30/088*** | (2023.01) |
| ***H10N 30/80*** | (2023.01) |
| ***H10N 30/857*** | (2023.01) |
| ***H10N 30/87*** | (2023.01) |
| ***H10N 30/88*** | (2023.01) |
| ***H10N 39/00*** | (2023.01) |
| *A61B 8/00* | (2006.01) |

(52) U.S. Cl.

CPC ......... *H10N 30/077* (2023.02); *H10N 30/088* (2023.02); *H10N 30/101* (2024.05); *H10N 30/802* (2023.02); *H10N 30/857* (2023.02); *H10N 30/878* (2023.02); *H10N 30/883* (2023.02); *H10N 39/00* (2023.02); *A61B 8/4209* (2013.01); *B06B 2201/76* (2013.01)

(56) References Cited

U.S. PATENT DOCUMENTS

| | | | |
|---|---|---|---|
| 11,998,950 | B2 * | 6/2024 | Bircumshaw ......... B06B 1/0651 |
| 2003/0127947 | A1 | 7/2003 | Chandran et al. |
| 2005/0156485 | A1 | 7/2005 | Gouk et al. |
| 2007/0222338 | A1 | 9/2007 | Aono et al. |
| 2008/0018199 | A1 | 1/2008 | Trolier-McKinstry et al. |
| 2008/0106400 | A1 | 5/2008 | Hunter et al. |
| 2008/0274607 | A1 | 11/2008 | Hyoung et al. |
| 2010/0256474 | A1 | 10/2010 | Faersnes et al. |
| 2011/0121915 | A1 | 5/2011 | Miller |
| 2012/0206014 | A1 * | 8/2012 | Bibl ...................... B06B 1/0207 310/330 |
| 2013/0086799 | A1 | 4/2013 | Biskeborn et al. |

* cited by examiner

MULTI-LAYERED TRANSDUCER

CROSS-REFERENCE TO RELATED APPLICATION

This application is a continuation of international application no. PCT/US2021/059193, filed on Nov. 12, 2021, which claims the benefit of U.S. Provisional Patent Application No. 63/113,094, filed on Nov. 12, 2020, each of which is incorporated by reference herein in its entirety.

BACKGROUND

Existing technologies for the manufacture of circuits rely on the mass manufacture of printed circuit boards (PCBs) or integrated circuits (ICs) which rely on "master" masks or tooling that is ill suited for mass customization, production of 2-D and 3-D conformable circuits (such that could be incorporated into performance athletic wear or athleisure attire).

SUMMARY

The present disclosure relates generally to transducers, their methods of manufacture and uses. In certain embodiments, the transducers may operate as electric potential sensors and/or acoustic sensors. The acoustic sensors may have a frequency range of 1 Hz to 24,000 Hz. The transducers acting as acoustic sensors may operate via a piezoresistive and/or optical force modality. In certain embodiments, the transducers may be formed by printing.

From one aspect, there is provided a transducer comprising a substrate layer, a first electrode layer on the substrate layer, a first piezoelectric layer on the first electrode layer, a second electrode layer on the first piezoelectric layer, a first electrical connector connected to the first electrode and a second electrical connector connected to the second electrode, one or both of the first electrical connector and the second electrical connector being connectable to an electronics circuit or to a ground.

In certain embodiments, the transducer can function as an electric potential sensor when the first piezoelectric layer is not polarized and can function as an acoustic sensor when the first piezoelectric layer is polarized.

In certain embodiments, the first piezoelectric layer is not polarized and wherein one of the first electrical connector and the second electrical connector is connected to an electronics circuit, and the other of the first electrical connector and the second electrical connector is floating, connected to ground, or connected to a shield. In certain embodiments, one or both of the first electrode and the second electrode layer may function as an insulator.

In certain embodiments, the first piezoelectric layer is polarized and wherein one of the first electrical connector and the second electrical connector is connected to an electronics circuit, and the other of the first electrical connector and the second electrical connector is floating, connected to ground, or connected to a shield.

In certain embodiments, the polarization of the first piezoelectric layer comprises application of more than 50 V/μm.

In certain embodiments, the substrate is flexible. In certain embodiments, the substrate is or elastic. In certain embodiments, the substrate comprises polyethylene terephthalate (PET). In certain embodiments, the substrate may comprise a textile, such as but not limited to a Goretex™.

In certain embodiments, an overall thickness of the transducer is less than about 160 μm.

In certain embodiments, a thickness of the first electrode layer is about 100 to about 600 nm, 200-600, 100-500, 100-400, 200-500, 200-400, optionally 400 nm.

In certain embodiments, a thickness of the second electrode layer is about 100 to about 400 nm.

In certain embodiments, a thickness of the first piezoelectric layer is about 4 to about 10 μm.

In certain embodiments, a thickness of the substrate is about 25 μm to about 150 μm. In certain embodiments, the thickness of the substrate layer is selected based on an optimization between ability of the transducer to bend and a support to the other layers of the transducer.

In certain embodiments, a thickness of one or both of the first electrical connector and the second electrical connector is about 8 μm.

In certain embodiments, the first piezoelectric layer comprises a piezoelectric composition including polyvinylidene fluoride.

In certain embodiments, one or both of the first and second electrodes have an electrode composition comprising poly(3, 4-ethylenedioxythioohene) polystyrene sulfonate (PEDOT:PSS).

In certain embodiments, one or both of the first electrical connector and the second electrical connector comprises an electrical connector composition comprising a metal, a metal alloy or a metal oxide.

In certain embodiments, the transducer further comprises an electronics circuit connected to one or both of the first electrical connector and the second electrical connector.

In certain embodiments, the electronics circuit includes a voltage amplifier, charge amplifier or current amplifier.

In certain embodiments, the transducer further comprises a processor connected to the electronics circuit for receiving signals detected by the transducer.

In certain embodiments, the processor is configured to filter the detected signals.

In certain embodiments, the transducer further comprises a display connected to the processor for displaying the detected signals or the filtered signals.

In certain embodiments, the transducer further comprising a metal shield around at least a portion of the transducer.

In certain embodiments, the transducer has a circumference which is quadrilateral, circular, or hexagonal.

In certain embodiments, the transducer has a surface area of about 70 to about 1500 $mm^2$. Example surface areas include 78, 314, 700 and 1250 $mm^2$.

In certain embodiments, the transducer was formed by printing, sequentially, the first electrode layer on the substrate layer, the first piezoelectric layer on the first electrode layer, the second electrode layer on the first piezoelectric layer.

In certain embodiments, one or more of the first piezoelectric layer, the first electrode layer and the second electrode layer are formed from a plurality of sub-layers.

In certain embodiments, the transducer further comprises a second piezoelectric layer on top of the second electrode layer and a third electrode layer on top of the second piezoelectric layer. In certain other embodiments, the transducer further comprises a third piezoelectric layer on top of the third electrode layer and a fourth electrode layer on top of the third electrode layer. Any of the first piezoelectric layer, the second piezoelectric layer and the third piezoelectric layer (when present) may be in contact with one another. In such cases, two piezoelectric layers that touch may also be considered as a single piezoelectric layer which is folded over. The third electrode may be a branch of the first or second electrode. The fourth electrode may be a branch of the first or second electrode.

In certain embodiments, one of the first piezoelectric layer and the second piezoelectric layer is polarized and the other of the first piezoelectric layer and the second piezoelectric layer is not polarized. In certain other embodiments, both of the first piezoelectric layer and the second piezoelectric layer are polarized. In certain other embodiments, both of the first piezoelectric layer and the second piezoelectric layer are not polarized. In certain other embodiments, the transducer comprises a plurality of polarized piezoelectric layers and a plurality of non-polarized piezoelectric layers. In other words, in certain embodiments, a single multi-layered transducer can function as both an acoustic and an electric potential sensor, or only as an acoustic sensor or only as an electric potential sensor.

In certain embodiments, the transducer further comprises a passivation (insulation) layer covering the second electrode layer. The passivation layer may function as a protective layer. The passivation layer may function as an insulating layer.

From another aspect, there is provided a plurality of transducers according to any of the embodiments described above. The first piezoelectric layer of at least two of the plurality of transducers can be: (i) both polarized, (ii) both non-polarized, and (iii) one is polarized and the other is non-polarized.

From another aspect, there is provided a sheet of material comprising a plurality of the transducers according to any of the embodiments described above. The plurality of the transducers may be arranged as an array on the sheet of material with any configuration. Each of the plurality of the transducers may have the same or different sensor function based on polarization or not of their piezoelectric layers. For example, one or more of the plurality of the transducers may function as acoustic sensors, and one or more of the plurality of the transducers may function as electric potential sensors. Alternatively, they may all function as acoustic sensors, or they may all function as electric potential sensors.

In certain embodiments, at least two of the plurality of transducers have different surface areas. In certain embodiments, the number of transducers on the sheet of material is optimized according to fitting a maximum number of transducers within a certain size range on the sheet of material.

In certain embodiments, the plurality of transducers share a common substrate layer.

From another aspect, there is provided a method of making a transducer, the method comprising: obtaining a substrate layer having a substrate composition; forming a first electrode layer, having an electrode composition, on the substrate layer; forming a first piezoelectric layer, having a piezoelectric composition, on the first electrode layer; and forming a second electrode layer, having an electrode composition, on the first piezoelectric layer.

In certain embodiments, forming the first electrode layer comprises printing the electrode composition followed by annealing. The printing may comprise screen printing through a mesh.

In certain embodiments, forming the first piezoelectric layer comprises printing the piezoelectric composition followed by annealing. The printing may comprise screen printing through a mesh.

In certain embodiments, forming the second electrode layer comprises printing the electrode composition followed by annealing. The printing may comprise screen printing through a mesh.

In certain embodiments, the method further comprises forming one or both of a first electrical connector associated with the first electrode layer and a second electrical connector associated with the second electrode layer, wherein one or both of the first electrical connector and the second electrical connector are printed after the first electrode layer and before the first piezoelectric layer.

In certain embodiments, the piezoelectric composition includes polyvinylidene fluoride.

In certain embodiments, the electrode composition comprises poly(3, 4-ethylenedioxythioohene) polystyrene sulfonate (PEDOT:PSS).

In certain embodiments, the substrate composition comprises PET.

In certain embodiments, one or both of the first electrical connector and/the second electrical connector comprises an electrical connector composition comprising a metal, a metal alloy or a metal oxide. One example is silver.

In certain embodiments, the method further comprises polarizing the piezoelectric layer by applying more than 50 V/μm.

In certain embodiments, the first piezoelectric layer is deposited over a larger area than the first electrode layer, the method further comprising trimming the first piezoelectric layer.

In certain embodiments, forming the first piezoelectric layer comprises printing a plurality of sub-layers of the first piezoelectric layer.

In certain embodiments, forming one or both of the first electrode layer and second electrode layer comprises printing a plurality of sub-layers of one or both of the first electrode layer and second electrode layer, respectively.

In certain embodiments, the method further comprises forming a second piezoelectric layer on top of the second electrode layer and forming a third electrode layer on top of the second piezoelectric layer.

In certain embodiments, the method further comprises forming a second piezoelectric layer on top of the second electrode layer and forming a third electrode layer on top of the second piezoelectric layer, wherein the first piezoelectric layer and the second piezoelectric layer may be (i) both polarized, (ii) both unpolarized, or (iii) one is polarized and the other is unpolarized.

In certain embodiments, the method further comprises forming a passivation layer covering the second electrode layer.

In certain embodiments, the method further comprises forming a plurality of the transducers wherein the plurality of transducers have a common substrate layer.

In certain embodiments, at least two of the transducers have a first electrode layer or a second electrode layer that share a connection to the ground or to the electrical circuit.

In certain embodiments, the method further comprises forming a plurality of the transducers on a sheet.

From another aspect, there is provided a transducer made according to any of the embodiments of the methods described above.

From a further aspect, there is provided use of any of the embodiments of the transducers or the plurality of transducers described herein, for detecting an acoustic signal and/or electric potential signal from a living body and/or an inanimate body.

In certain embodiments, the use comprises non-contact with the living body and/or the inanimate body.

In certain embodiments, the use comprises contact with the living body and/or the inanimate body. In certain embodiments, the contact is through clothing of the living body.

In certain embodiments, the transducer may be incorporated into a clothing, headwear, footwear, eyewear, headwear, bandage, bandaid, sticker, blanket, accessory, watch, device. From another aspect, there is provided one or a clothing, headwear, footwear, eyewear, headwear, bandage, bandaid, sticker, blanket, accessory, watch, device, incorporating any of the embodiments of the transducer described herein.

In certain embodiments of the use of the transducer, the transducer is oriented such that an electric potential functioning side of the transducer is facing the living or non-living body. Uses of such transducers include, but are not limited to, monitoring of conditions of a body. This could be for any purpose such as for management, prevention and/or diagnosis of a condition or a state, characterizing a condition, maintaining a condition, enhancing a condition, preventing disease or damage. In this respect, they can be suitable for general use. In certain embodiments, the transducers are noninvasive. The transducers can be used for one or both of contact or contact-free uses.

In certain embodiments of the printable transducer and its uses, the transducer can be incorporated into wearables, such as but not limited to clothing, head wear, masks, eye wear, accessories, skin patches, bandages, footwear, wearable devices, blankets. The clothing may be a whole-body configuration or partial body covering. In this respect, the printable transducer may be shape-conforming to conform to a profile of the body. In this respect, the transducers can be considered as which are readily adaptable for inclusion in garments. In certain embodiments, the transducers may provide continuous monitoring of medical/wellness/fitness parameters such as heart rate, breath rate, movement, temperature, wound pH, as non-limiting examples.

In certain embodiments, the transducers can be fabricated in unison with the clothing or the textile material that such clothing comprise.

In other embodiments, the printable transducers may be used for non-destructive continuous monitoring and/or predictive maintenance detection of oil pipe failure, monitoring HVAC performance efficiency, water leaks, rotating parts resilience, imprinting, transparent antennas printed onto glass, etc. The transducers may function as electric potential sensors (capacitive sensors) and/or acoustic sensors (piezoresistive sensors, piezoelectric sensors, and/or optical force sensor).

In certain embodiments, the transducers may have a flexible sticker form factor, and may include mounted integrated circuits. Some uses comprise remote monitoring of packages and industrial equipment, to name a few.

In yet other embodiments, the methods of the present technology may be used to manufacture 3-D stacked circuits, radio frequency antennas for mobile devices, electromagnets, motors, actuators, electromechanical, piezoelectric, piezo mechanical and piezo acoustic devices. Any of these may be manufactured to have a conformable property.

Advantageously, in certain embodiments described herein, the method of making the transducers is efficient, simple and flexible. In terms of the flexibility of the method, it is possible to make an electric potential transducer and an acoustic transducer with common method steps and materials. In certain embodiments, a polarization step of the piezoelectric material is the only difference. This clearly provides efficiencies at an industrial manufacturing plant where the same facilities can be used to make sensors with different functionalities. In certain embodiments, electric potential transducers and acoustic transducers may be interwoven for flexible placement and/or efficient multi-modal data fusion.

In certain embodiments, the method can be used to manufacture sensors with non-intuitive acoustic, mechanical, optical, magnetic, or electric properties using one or more of the layers described herein.

In the context of the present specification, unless expressly provided otherwise, by "body" is meant (i) a living subject, such as a human or animal, or (ii) a non-living object such as a man-made equipment/machinery or structure (e.g. building, bridge, dam, power generator, turbine, battery, heating/ventilation/air conditioning (HVAC) systems, internal combustion engines, jet engines, aircraft wing, environmental infrasound, ballistics, drones and/or seacrafts, nuclear reactors, other mechanical, electrical, aerodynamic, hydrodynamic, devices or geological formations).

In the context of the present specification, unless expressly provided otherwise, by animal is meant an individual animal that is a mammal, bird, or fish. Specifically, mammal refers to a vertebrate animal that is human and non-human, which are members of the taxonomic class Mammalia. Non-exclusive examples of non-human mammals include companion animals and livestock. Animals in the context of the present disclosure are understood to include vertebrates. The term vertebrate in this context is understood to comprise, for example, fishes, amphibians, reptiles, birds, and mammals including humans. As used herein, the term "animal" may refer to a mammal and a non-mammal, such as a bird or fish. In the case of a mammal, it may be a human or non-human mammal. Non-human mammals include, but are not limited to, livestock animals and companion animals.

In the context of the present specification, unless expressly provided otherwise, by "remote" or "contact-free" is meant that certain components of the system do not have direct contact with the body. "Remote" or "contact-free" includes situations in which certain components of the system are spaced from the body, such as by air. There is no limitation on a distance of the spacing. "Remote" or "contact-free" in the context of embodiments of the present system includes signal detection "over clothing" and/or "through clothing". For example, if the body is a human or animal subject, "remote" or "contact-free" means that certain components of the sensor system do not directly contact the skin/hair, clothing covering the skin/hair or fur.

In the context of the present specification, unless expressly provided otherwise, by "bodily condition" is meant a health or physical condition of a body. For non-living bodies, the bodily condition may include a physical state of the body. For example, a structural integrity, crack development, battery life, environmental noise pollution, rotating motor engine performance optimization, surveillance etc. For living bodies, the bodily condition may refer to, but is not limited to, one or more of: an identity of the human or animal, a category of the human or animal, a viral infection, a bacterial infection, a heart beat, chest pain and underlying causes, an inhale, an exhale, a cognitive state, a reportable disease, a fracture, a tear, an embolism, a clot, swelling, occlusion, prolapse, hernia, dissection, infarct, stenosis, hematoma, edema, contusion, osteopenia and presence of a foreign body in the subject such as an improvised explosive device (IED), surgically implanted improvised explosive device (SIIED), and/or body cavity bomb (BCB). Examples of viral infections include but are not limited to infections of Covid-19, SARS, influenza. Reportable diseases are diseases considered to be of great public health importance and include: Anthrax, Arboviral diseases (diseases caused by viruses spread by mosquitoes, sandflies, ticks, etc.) such as West Nile virus, eastern and western equine encephalitis, Babesiosis, Botulism, Brucellosis, Campylobacteriosis, Chancroid, Chickenpox, *Chlamydia*, Cholera, Coccidioidomycosis, Cryptosporidiosis, Cyclosporiasis, Dengue virus infections, Diphtheria, Ebola, Ehrlichiosis, Foodborne disease outbreak, Giardiasis, Gonorrhea, *Haemophilus* influenza, invasive disease, Hantavirus pulmonary syndrome, Hemolytic uremic syndrome, post-diarrheal, Hepatitis A, Hepatitis B, Hepatitis C, HIV infection, Influenza-related infant deaths, Invasive pneumococcal disease, Lead—elevated blood level, Legionnaire disease (legionellosis), Leprosy, Leptospirosis, Listeriosis, Lyme disease, Malaria, Measles, Meningitis (meningococcal disease), Mumps, Novel influenza A virus infections, Pertussis, Pesticide-related illnesses and injuries, Plague, Poliomyelitis, Poliovirus infection, nonparalytic, Psittacosis, Q-fever, Rabies (human and animal cases), Rubella (including congenital syndrome), *Salmonella paratyphi* and *typhi* infections, *Salmonellosis*, Severe acute respiratory syndrome-associated coronavirus disease, Shiga toxin-producing *Escherichia coli* (STEC), Shigellosis, Smallpox, Syphilis, including congenital syphilis, Tetanus, Toxic shock syndrome (other than streptococcal), Trichinellosis, Tuberculosis, Tularemia, Typhoid fever, Vancomycin intermediate *Staphylococcus aureus* (VISA), Vancomycin resistant *Staphylococcus aureus* (VRSA), Vibriosis, Viral hemorrhagic fever (including Ebola virus, Lassa virus, among others), Waterborne disease outbreak, Yellow fever, Zika virus disease and infection (including congenital). Examples of underlying causes behind chest pain which may be considered as a bodily condition include one or more of muscle strain, injured ribs, peptic ulcers, gastroesophageal reflux disease (GERD), asthma, collapsed lung, costochondritis, esophageal contraction disorders, esophageal hypersensitivity, esophageal rupture, hiatal hernia, hypertrophic cardiomyopathy, tuberculosis, mitral valve prolapse, panic attack, pericarditis, pleurisy, pneumonia, pulmonary embolism, heart attack, myocarditis, angina, aortic dissection, coronary artery dissection, pancreatitis, and pulmonary hypertension.

Variations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Figure 1:
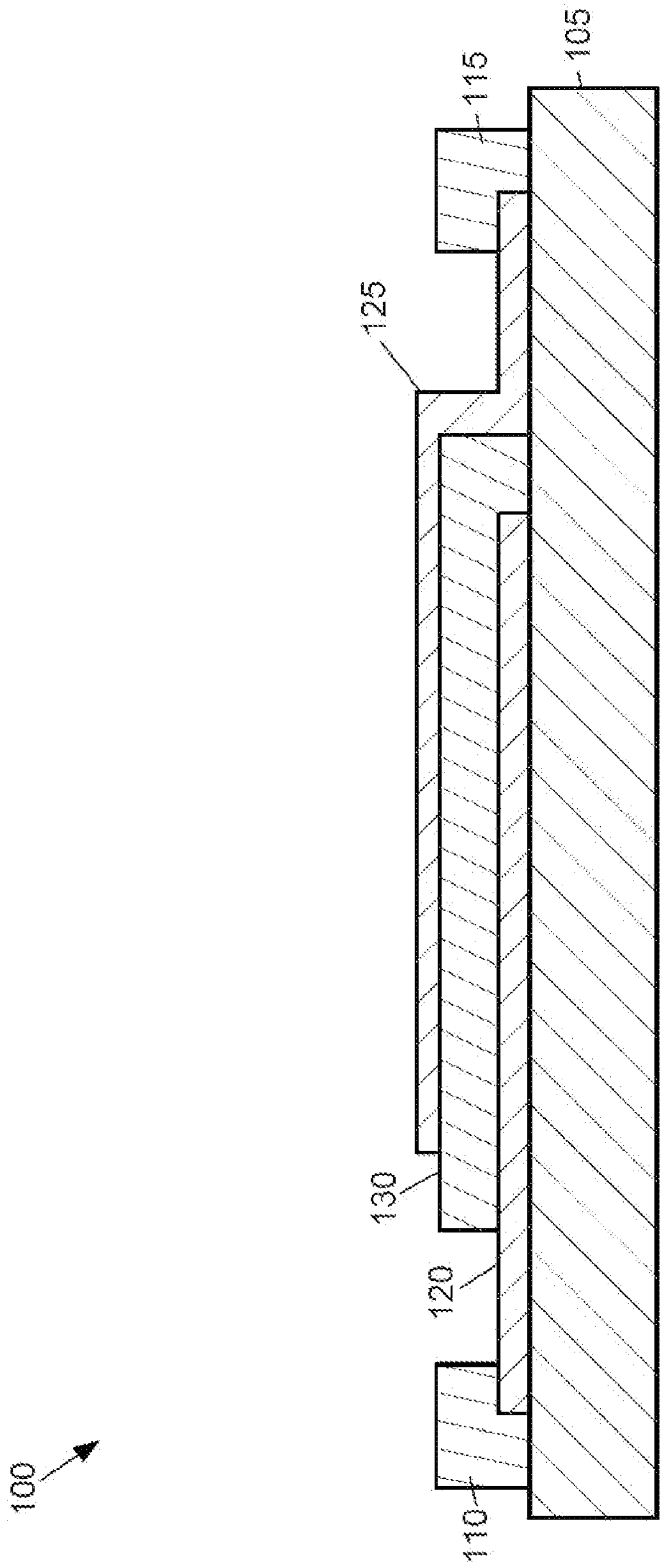
FIG. 1 is a diagram of a transducer in accordance with various embodiments of the present technology.

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudo-code, and the like represent various processes which may be substantially represented in computer-readable media and so executed by a computer or processor, whether or not such computer or processor is explicitly shown.

The functions of the various elements shown in the figures, including any functional block labeled as a "processor," may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some embodiments of the present technology, the processor may be a general purpose processor, such as a central processing unit (CPU) or a processor dedicated to a specific purpose, such as a digital signal processor (DSP). Moreover, explicit use of the term a "processor" should not be construed to refer exclusively to hardware capable of executing software, and may implicitly include, without limitation, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown. Moreover, it should be understood that one or more modules may include for example, but without being limitative, computer program logic, computer program instructions, software, stack, firmware, hardware circuitry, or a combination thereof.

Aspects of the present technology are directed to printable transducers, their method of manufacture and uses. Such transducers can be incorporated into many different form factors and incorporated into different multi-component systems.

In certain embodiments, some such uses includes the monitoring, characterizing, enhancing or preventing of a condition of an animal body, such as a human. Long-term measurement and monitoring of vital signs, e.g., time and frequency domain Heart rate (HR), HR variability (HRV), respiratory rate (RR), RR variability (RRV), full bandwidth PCG (phonocardiogram), APG (acceleration phonocardiogram), BCG (ballistocardiogram), SCG (seismocardiogram), STT (slope transit time), PTT (pulse transit time), PEP (pre-ejection period), PAT (pulse arrival time), S1 (first heart sound), S2 (second heart sound resting heart rate), TD (time interval between the J peak in the BCG signal and the systolic peak in the PPG signal), VTT (vascular time interval), body temperature, systolic and diastolic blood pressure, etc., provides early detection to facilitate the promise for the early treatment potential problems and/or chronic disease exacerbation, especially for older adults. Compared with the many wearable heartrate monitoring systems available, embodiments of the transducers of the present technology configured as flexible multistable mechanical wearable metamaterials provide a next generation of monitoring devices which are unintrusive and comfortable. Such systems including embodiments of the present transducers can detect and monitor, whether continuously or not, signals from the animal body generated, for example, by the sudden ejection of blood into the large vessels at each cardiac cycle, lung function, and gut peristaltic motion.

Other uses include monitoring of conditions and well-being in older humans, chronic disease regulation, and management of independent living for older adults.

Further uses include the continuous, non-intrusive monitoring of vital signs of elite and warrior athletes for performance enhancement.

Compared with other methods such as electrocardiography (ECG), transducers of the present technology do not require electrodes or fasteners to be affixed to the body and thus its uses are ideal for long term in-home and activity monitoring.

Furthermore, transducers of the present technology can be combined with carrier materials to maximize saliency and manage the large variability in BCG/SCG signal in order to enable full characterization, detection and monitoring of whole-body and whole-system functional state with equal if not better resolution to a wet electrode ECG. This technology can be adapted to diagnose any other condition disclosed herein in other animals, as well as plants and fungi.

Additionally, embodiments described herein can be used for ascertaining the status of inanimate objects such as roads, bridges, engines, houses, building, or other devices and structures described herein. For example, continuous monitoring is important for renewable energy systems, hybrid-electric vehicles, locomotives, space missions, etc. One common but major concern in these aforementioned systems is reliability, which is responsible for economic or safety considerations. As an example, in photovoltaic (PV) power generation systems, low reliability increases maintenance costs and decreases system availability, and therefore, increase the levelized cost of electricity (LCOE), which affects the marketplace. A similar issue exists in offshore wind farms, which is not conveniently or inexpensively accessible for maintenance. In automobile, locomotive, and avionic applications, safety requirements impose nearly zero failure tolerance. Since, failure is never completely preventable, the preferred way is to predict the where, when, and how of failure and take action before a failure occurs. Continuous lifetime monitoring combined with accurate domain-adaptable ML/AI predictive algorithms, if performed appropriately, can fulfill this mission. We have developed transducers with one or more of piezo-resistive, piezo-electrical, and/or capacitive field effect that provide next generation unintrusive continuous monitoring for the prediction of product and structural reliability. Our solutions are combined within a domain adaptable software infrastructure that provides actionable insights from test structure data to integrate predicted and observed times to failure to a probability distribution that is continuously updated and extrapolated to targeted small failure probabilities. Consequently, the probability distribution for the (small) test structure size can be up-extrapolated to the corresponding distribution for the (larger) product size, or down-extrapolated in the opposite direction.

Described herein are at least four methodologies for the manufacturing of novel sensors and structures. These methodologies include:

1. Fabrication of new flexible single layer Piezo sensors with improved design
2. Polarization and characterization of new flexible single layer sensors
3. Fabrication and polarization of flexible multi-layer Piezo sensors with improved design 4. Impregnation and optimization of 3D/4D printing to solve both mechanical and electrical challenges of shape-shifting auxetic metamaterials Described herein are various methods for the manufacture of 3-D shape shifting auxetic metamaterials by additive manufacturing methods combined with 2-D silkscreen and/or inkjet printing. Materials used these methods or incorporated into the transducers comprise one or more of, for example, Metallic thin films, Conductive and insulating thermoplastics, Conductive and insulating inks, Conductive pastes, Conductive photopolymers and conductive polymers, Graphene, carbon nanotubes (CNTs), nanowires, particles, Polyvinylidene Fluoride (PVDF) film sensors.

Transducer

According to certain aspects and embodiments of the present technology, a transducer 100 may be manufactured, such as using the method 400 which is described in further detail below. The transducer 100 includes a substrate layer 105, a first electrode layer 120, a second electrode layer 125, a piezoelectric layer 130, a first electrical connector 110, and/or a second electrical connector 115, in certain embodiments. The transducer 100 may be printed on the substrate layer 105, such as using a screen-printing and/or ink-jet printing process. Using a screen-printing and/or ink-jet printing process may optimize and/or increase flexibility, performance, and product reliability.

The transducer 100 may act as one or more of an acoustic sensor or an electric potential sensor. The transducer 100 acting as an acoustic sensor may operate via a piezoresistive and/or optical force modality. In certain embodiments, the transducer 100 may have multiple functionalities. The function of the transducer 100 may be determined based on how and/or whether a piezoelectric layer 130 of the transducer 100 is polarized. Multiple transducers 100 may be formed on a sheet of the substrate layer 105. The transducers 100 sharing the same substrate layer may have the same or different sensor functions.

The substrate layer 105 may be flexible and/or elastic. During use of the transducer 100, the substrate layer may be placed against the user's skin, held close to the skin or be incorporated in a piece of clothing, headwear, footwear, eyewear, accessory, blanket, bandaid, bandage or the like. Accordingly, the substrate layer 105 may be made of a biocompatible material that will not irritate or otherwise damage the user's skin.

The substrate layer 105 is composed of a substrate substance. The substrate substance may comprise any one or combination of polyethylene terephthalate (PET), polyester, mylar, kapton, polytetrafluorethylene, surface modified polytetrafluoroethylene, expanded polytetrafluoroethylene, surface modified expanded polytetrafluoroethylene, low density polyethylene, medium density polyethylene, polyvinylidene, cellulose acetate, cellulose nitrate, polyimide, polydimethylsiloxane, SiO2-PET, and/or SiNx-kapton. A polytetrafluroethylene type substrate may be surface modified to enable adhesion of deposited films by plasma treatment, sodium etching, and/or any other suitable method for improving adhesion.

The thickness of the substrate layer 105 may range from about 25 μm to about 150 μm, about 50 μm to about 150 μm, about 75 μm to about 150 μm, and/or about 100 μm to about 150 μm. In certain embodiments, the thickness of the substrate layer is about 125 μm.

The first electrode layer 120 may be formed on the substrate layer 105 such as by printing. The piezoelectric layer 130 may be formed on the first electrode layer 120 such as by printing. The second electrode layer 125 may be formed on the piezoelectric layer 130 such as by printing.

The first electrode layer 120 and/or second electrode layer 125 may have a thickness of about 100 to about 600 nm. The first electrode layer 120 and second electrode layer 125 may have a same thickness, such as about 400 nm. In other embodiments, the first electrode layer 120 and the second electrode layer 125 may have a different thickness.

In certain embodiments, the first electrode layer 120 and the second electrode layer 125 are formed of an electrode composition comprising poly(3, 4-ethylenedioxythioohene) polystyrene sulfonate (PEDOT:PSS). In other embodiments, the first electrode layer 120 and the second electrode layer 125 may be formed of different electrode compositions. Other electrode compositions of the first electrode layer 120 and/or second electrode layer 125, without limitation, include graphene, thin film gold, thin film indium, carbon nanotube, and/or silver nanowire dispersions. One or both of the first electrode layer 120 and the second electrode layer 125 may be optically transparent, translucent or opaque.

The piezoelectric layer 130 is positioned between the first electrode layer 120 and the second electrode layer 125. The piezoelectric layer 130 is in contact with the first electrode layer 120 and the second electrode layer 125. The piezoelectric layer 130 may have a thickness of about 4 to about 10 μm. A variation of the thickness of the piezoelectric layer (in other words a surface roughness) may be less than about 2000 nm, or less than about 1000 nm.

The piezoelectric layer 130 is formed of a piezoelectric composition. The piezoelectric composition may comprise polyvinyl fluoride and/or co-trifluoroethylene. The piezoelectric composition may comprise about 80 percent by weight polyvinyl fluoride and/or about 20 by weight co-trifluoroethylene.

The transducer 100 may have a first electrical connector 110, and/or a second electrical connector 115. The first electrical connector 110 may be connected to the first electrode layer 120. The second electrical connector 115 may be connected to the second electrode layer 125. The first electrical connector 110 and/or second electrical connector 115 may be formed of a composition that includes silver and/or any other conductive material. The composition forming the first electrical connector 110 and/or second electrical connector 115 may be a polymer composition.

The first electrical connector 110 and/or second electrical connector 115 may have a thickness of about 0.25 to 1 μm, 1 to 2 μm, 2 to 4 μm, 4 to 6 μm, 6 to 8 μm, 8 to 10 μm, 10 to 12 μm, 12 to 14 μm, 14 to 16 μm, 16 to 18 μm, 18 to 20 μm, 20 to 25 μm, and/or 25 to 30 μm. In certain embodiments, the thickness of the first electrical connector 110 and/or second electrical connector 115 is about 8 μm.

Figure 6:
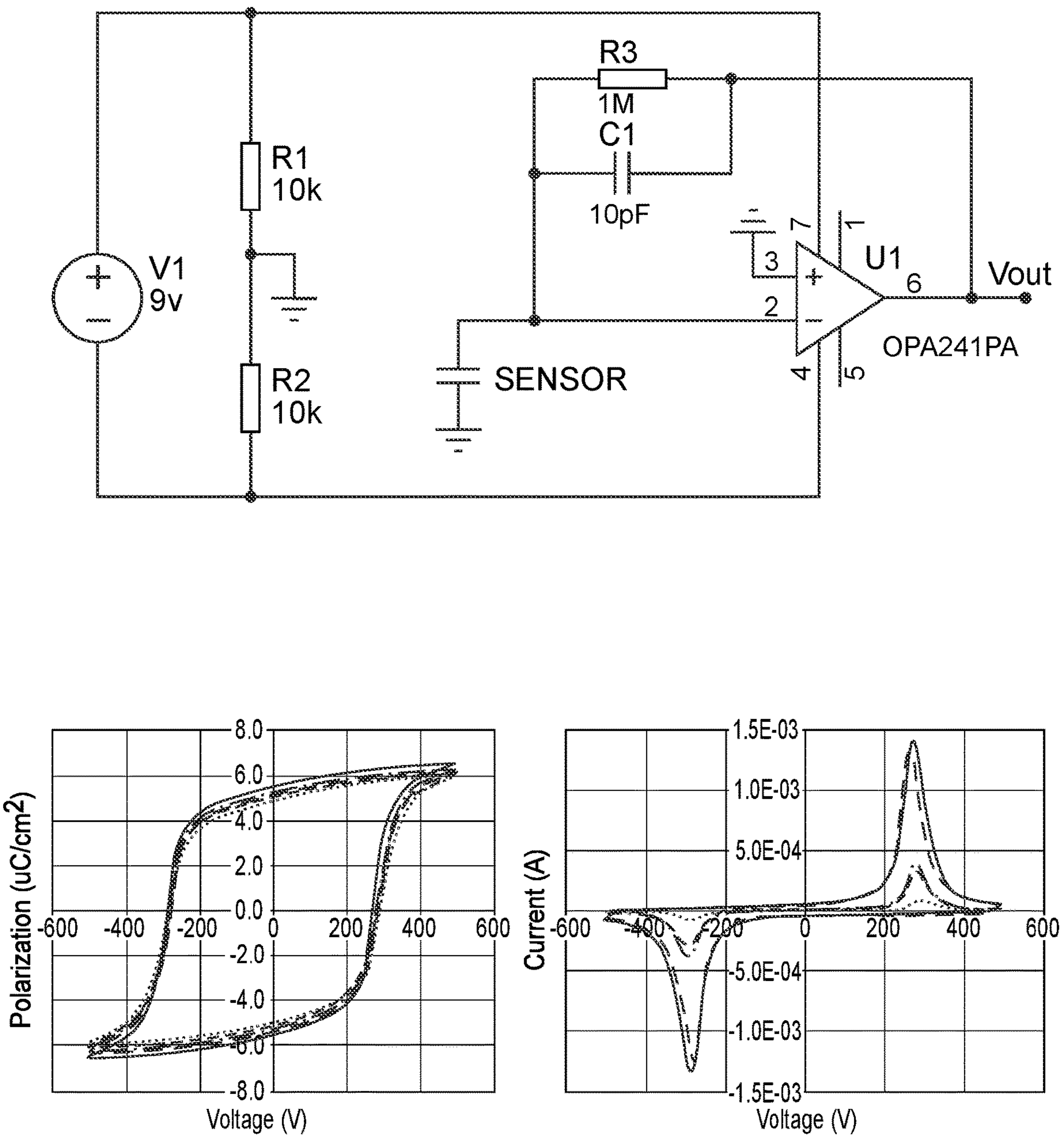
FIG. 6 is a diagram of an electric circuit containing a sensor in accordance with various embodiments of the present technology.

An electronics circuit may be connected to the first electrode layer 120, such as via the first electrical connector 110. The electronics circuit may be any suitable electronics circuit for collecting signals from the first and second electrodes. FIG. 6 illustrates an exemplary circuit that includes the transducer 100. The electronics circuit may include an amplifier, such as a charge amplifier and/or a voltage amplifier. A processor may be connected to the electronics circuit. The processor may receive signals detected by the transducer 100. The processor may be configured to filter the signals. The processor may be in communication with a display, and may output an interface to the display. The interface may be generated based on the signals received from the transducer 100. The interface may display the signals received from the transducer 100 or the filtered signals from the processor.

The transducer 100 may be covered and/or surrounded by an insulating layer (also referred to as "passivation layer" herein). In certain embodiments, the insulating layer is formed of the same material as the substrate layer 105. In other embodiments, the insulating layer may be made of another material. For example, in some embodiments, the insulating layer is made of a material that protects the second electrode or another uppermost electrode. In other embodiments, the insulating layer is made of a material that has a shielding effect from electric or acoustic signals. In yet other embodiments, the insulating layer may be optically transparent or translucent.

The transducer 100 may be surrounded by a shield, such as a metal shield around a circumference of the transducer 100. Alternatively, the shield may extend over the second electrode, another uppermost electrode (when present) or the insulting layer (when present). The metal shield may or may not be placed against the skin of the user.

The transducer 100 may be any shape, such as a quadrilateral shape, a circular shape, or a hexagonal shape. The transducer 100 may have a surface area of about 70 to about 1500 $mm^2$, such as 78 $mm^2$, 314 $mm^2$, 700 $mm^2$, or 1250 $mm^2$. The transducer 100 may have a thickness of about 10 mm to 20 mm, 20 mm to 30 mm, 30 mm to 40 mm, 40 mm to 50 mm, 50 mm to 60 mm, 60 mm to 70 mm, 70 mm to 80 mm, 80 mm to 90 mm, 90 mm to 100 mm, 110 mm to 120 mm, 120 mm to 130 mm, 130 mm to 140 mm, 140 mm to 150 mm, and/or 150 mm to 160 mm.

Figure 7:
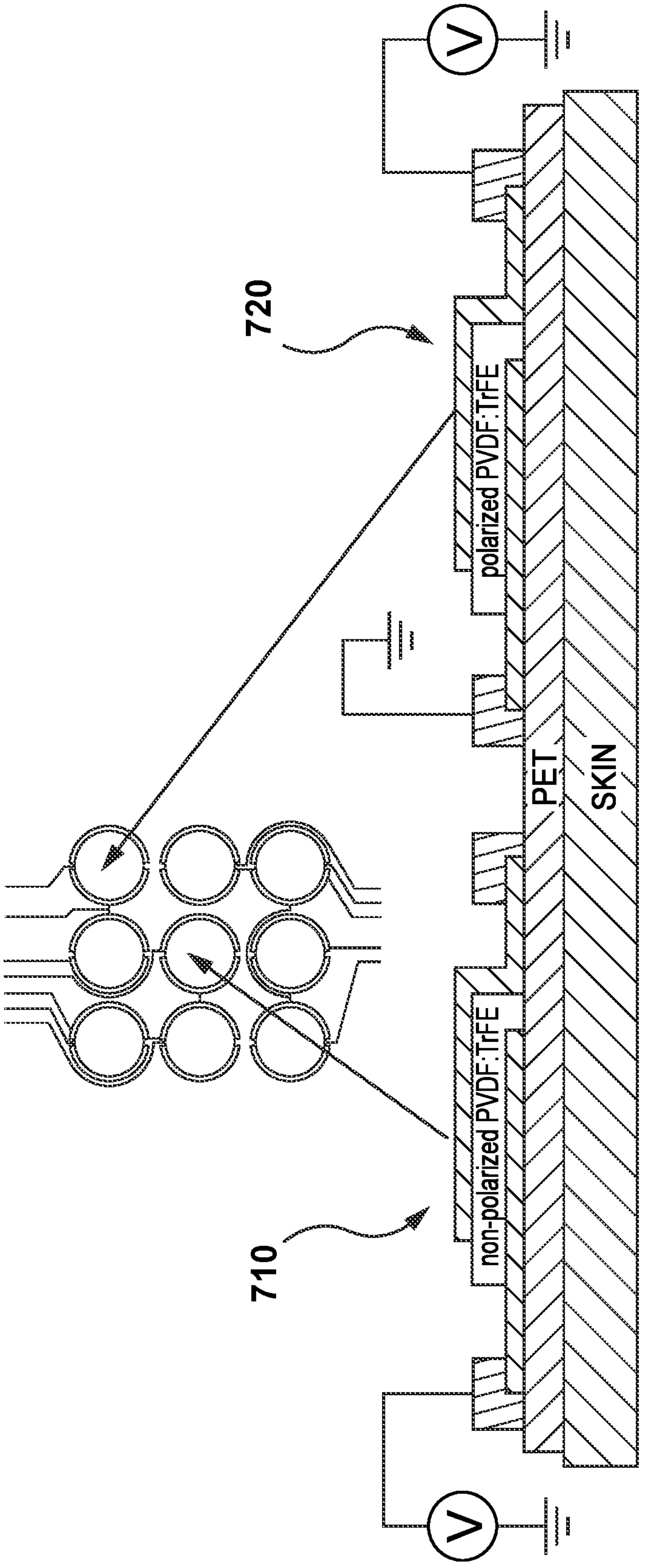
FIG. 7 is an example of an array of transducers in accordance with various embodiments of the present technology.

An array of the transducers 100 may be formed, such as a 3×3 array of transducers 100. Some of the transducers 100 in the array may act as electric potential sensors, and some may act as acoustic sensors. In certain embodiments, some of the transducers 100 in the array may act as both electric potential sensors and acoustic sensors as will be described further below. Each transducer 100 in the array may be poled individually in order to configure the function of the individual transducer 100. In certain embodiments, the transducers 100 of the array share the same substrate layer. At least some of the transducers 100 may also share a same ground connection. FIG. 7 illustrates an example of an array of transducers 100. The array in FIG. 7 includes both a transducer 710 acting as an electric potential sensor and a transducer 720 acting as an acoustic sensor.

Transducer—Additional Electrode Layers

Figure 2:
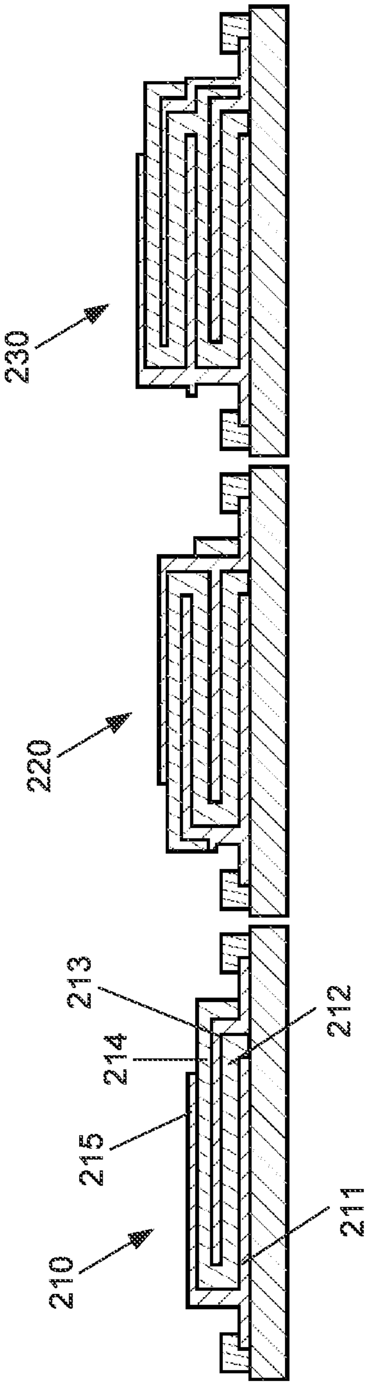
FIG. 2 is a diagram of transducers with multiple layers in accordance with various embodiments of the present technology.

FIG. 2 illustrates various other configurations of the transducer 100. Transducers 210, 220, and 230 are similar to the transducer 100, but have additional electrode layers and piezoelectric layers. As illustrated in FIG. 2, the transducers 210, 220, and 230, may contain a third electrode layer and optionally a fourth electrode layer. The first and third electrode layers may be connected through the same electrical connector and thus function in the same or similar manner. In this respect, the first and third electrodes may be considered as branches of the same electrode layer. Similarly, the second and fourth electrode layers may be connected through the same electrical connector and thus function in the same or similar manner. In this respect, the second and fourth electrodes may be considered as branches of the same electrode layer.

In other embodiments, each of the electrode layers may be connected to a separate electrical connector.

The transducers 210, 220, and 230 each contain multiple piezoelectric layers 130. For example, there are four piezoelectric layers 130 in the transducer 230 (first, second, third and fourth piezoelectric layers). The transducer 210 has a first electrode layer 211, a first piezoelectric layer 212, a second electrode layer 213, a second piezoelectric layer 214, and a third electrode layer 215.

The transducers 210, 220, and 230 are examples of alternative configurations of the transducer 100, but it should be understood that the transducer 100 may be manufactured with any number of additional electrodes and/or piezoelectric layers. In each configuration of the transducer 100, the first electrode layers 120 and second electrode layers 125 may alternate such that each piezoelectric layer is sandwiched between a first electrode layer and a second electrode layer. The multiple piezoelectric layers, when present, may contact one another. In such cases, the piezoelectric layer may be considered as a single layer which is folded on itself with an electrode positioned in the fold. In other embodiments, the multiple piezoelectric layers, are isolated from one another.

Transducer Shapes

Figure 3:
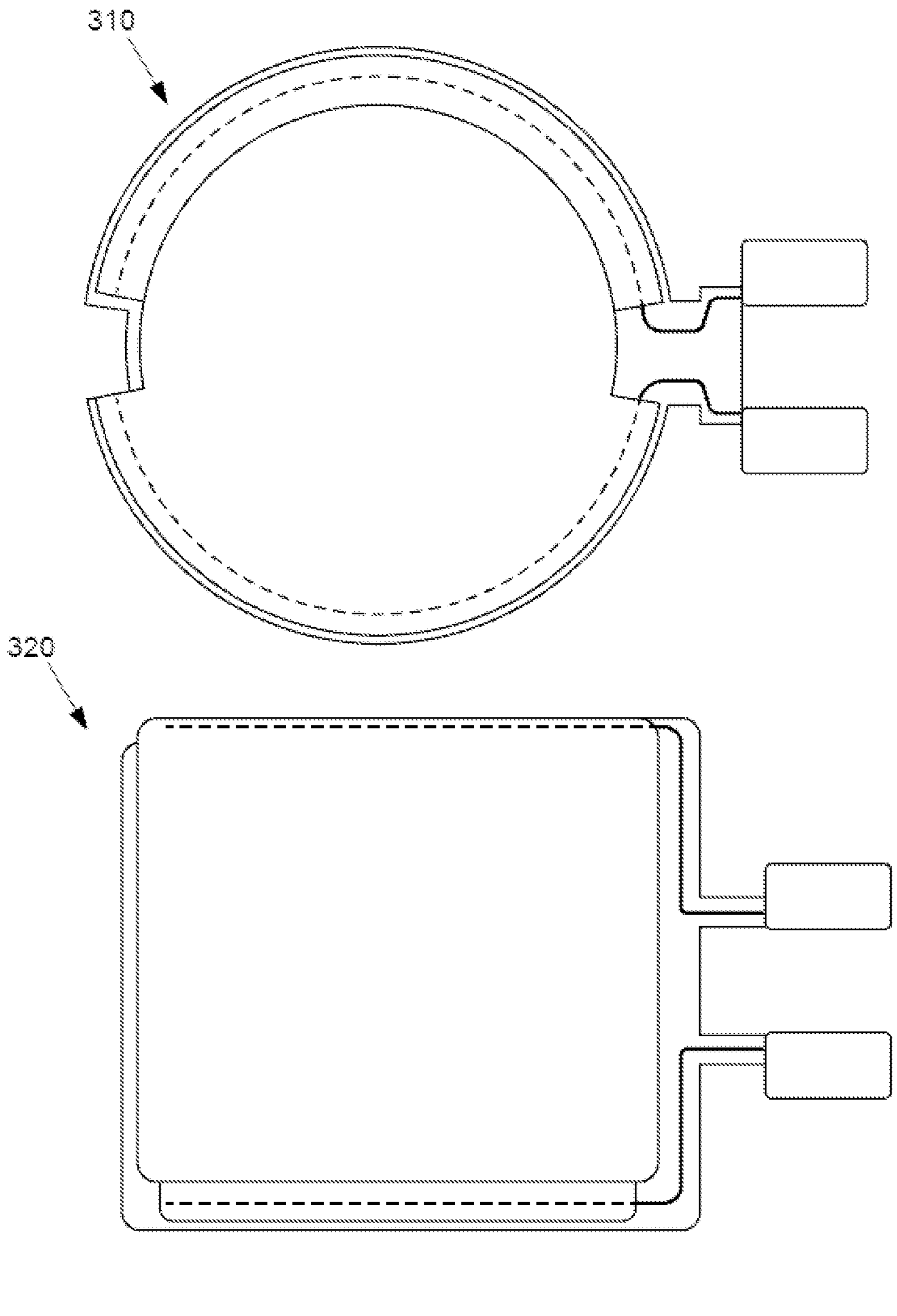
FIG. 3 is a diagram of shapes of transducers in accordance with various embodiments of the present technology.
Figure 5:
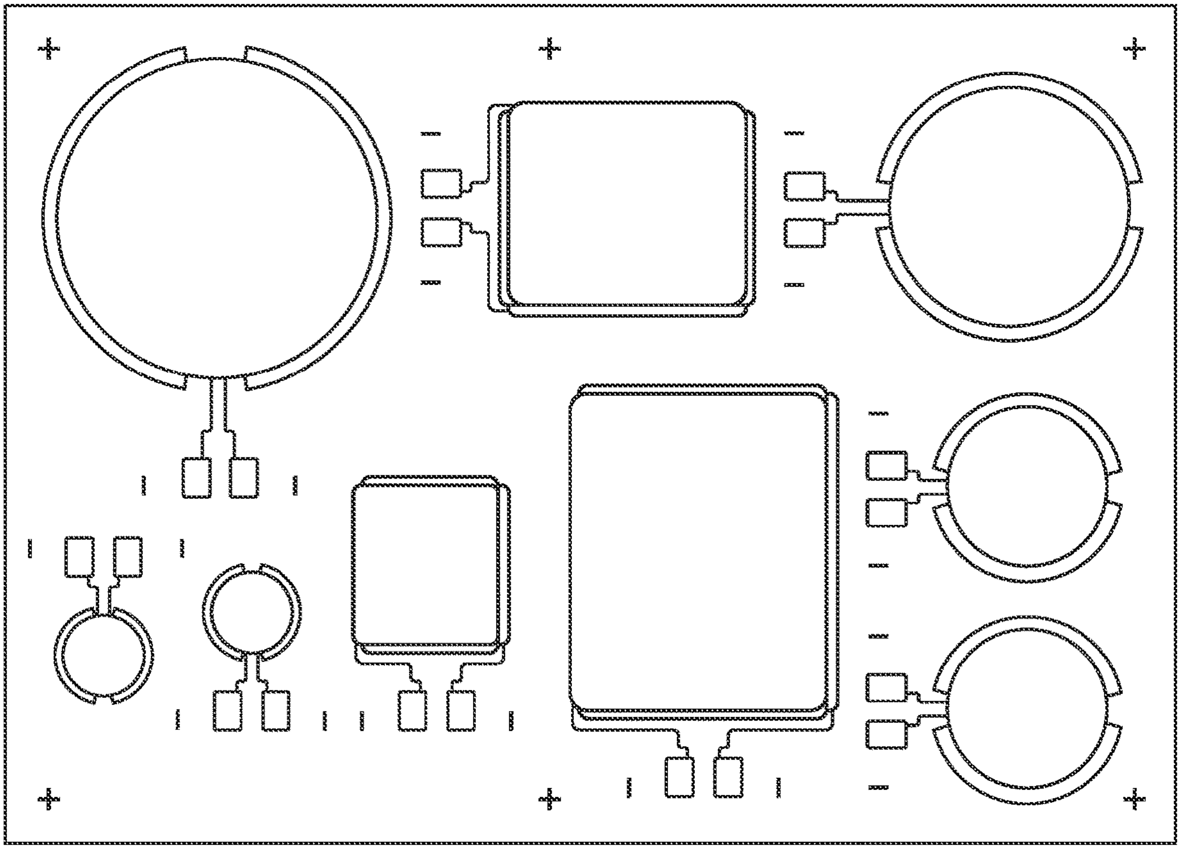
FIG. 5 is a diagram of additional shapes of transducers in accordance with various embodiments of the present technology.

FIG. 3 illustrates exemplary shapes of the transducer 100. FIG. 5 illustrates additional exemplary shapes of the transducer 100. It will be understood that the transducer has a larger surface area in an x-y direction than in the z direction. In other words, the transducer 100 has a substantially flat configuration. A circumferential shape of the transducer 100 is not limited and may have any configuration such as circular (circular transducer 310), square (square transducer 320), and/or rectangular.

Electric Potential Sensor

The transducer 100 may function as an electric potential sensor when the piezoelectric layer 130 is not polarized. In this arrangement, in which the piezoelectric layer 130 is not polarized, the piezoelectric layer 130 may act as an insulator between the two electrode layers 120 and 125.

Both of these electrode layers 120 and 125 may act as electrodes for collecting charges when the polarized piezoelectric layer 130 is vibrating. The second electrode layer 125 above the piezoelectric layer 130 may collect electric potential signals. The first electrode layer 120 below the piezoelectric layer 130 may act as a ground and/or shield. The first electrode layer 120 may act as an active shield.

The second electric layer 125 may be connected to a ground, may be floating, and/or may be connected to another signal for shielding. The first electrical connector 110 may connect the first electrode layer 120 to an electronics circuit.

Acoustic Sensor

The transducer 100 may function as an acoustic sensor when the piezoelectric layer 130 is polarized. When the transducer 100 is bent a potential difference may be created.

The second electrical connector 115 may connect the second electrode layer 125 to an electronics circuit. The first electrode layer 120 may be grounded via the first electrical connector 110. Alternatively, the second electrode layer 125 may be grounded via the second electrical connector 115 and/or the first electrode layer 120 may be connected to the electronics circuit via the first electrical connector 110.

Figure 8:
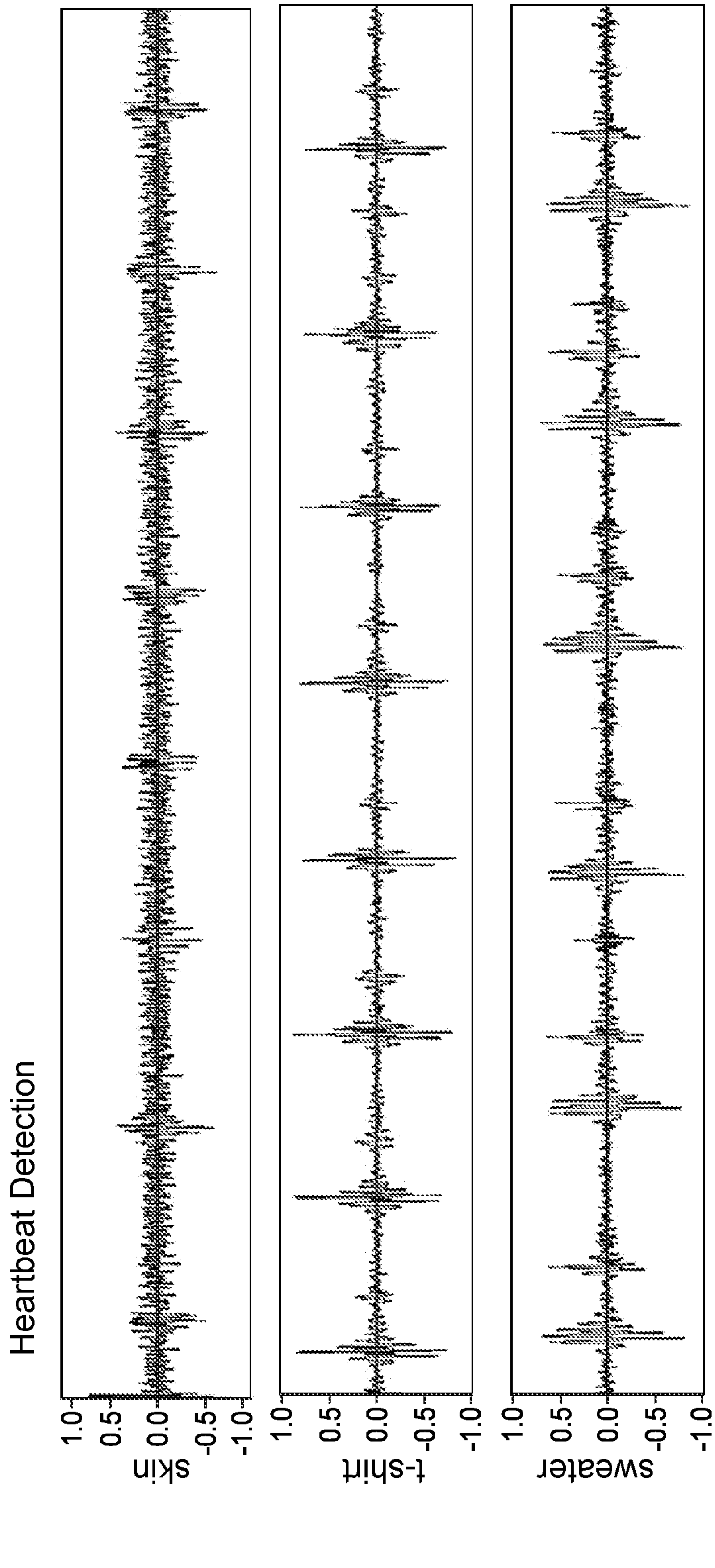
FIG. 8 is an example of signal data collected by a transducer in an acoustic configuration in accordance with various embodiments of the present technology.

FIG. 8 illustrates an example of data collected using the transducer 100 in the acoustic configuration. The transducer 100 was held on the chest area of the user. The data in FIG. 8 includes heartbeat data collected when the transducer 100 is placed against the user's skin, a shirt worn by the user, and a sweater worn by the user. The data showed that heart sounds can be detected through clothing of different thicknesses. The measurements confirmed a heartrate of the user.

Figure 9:
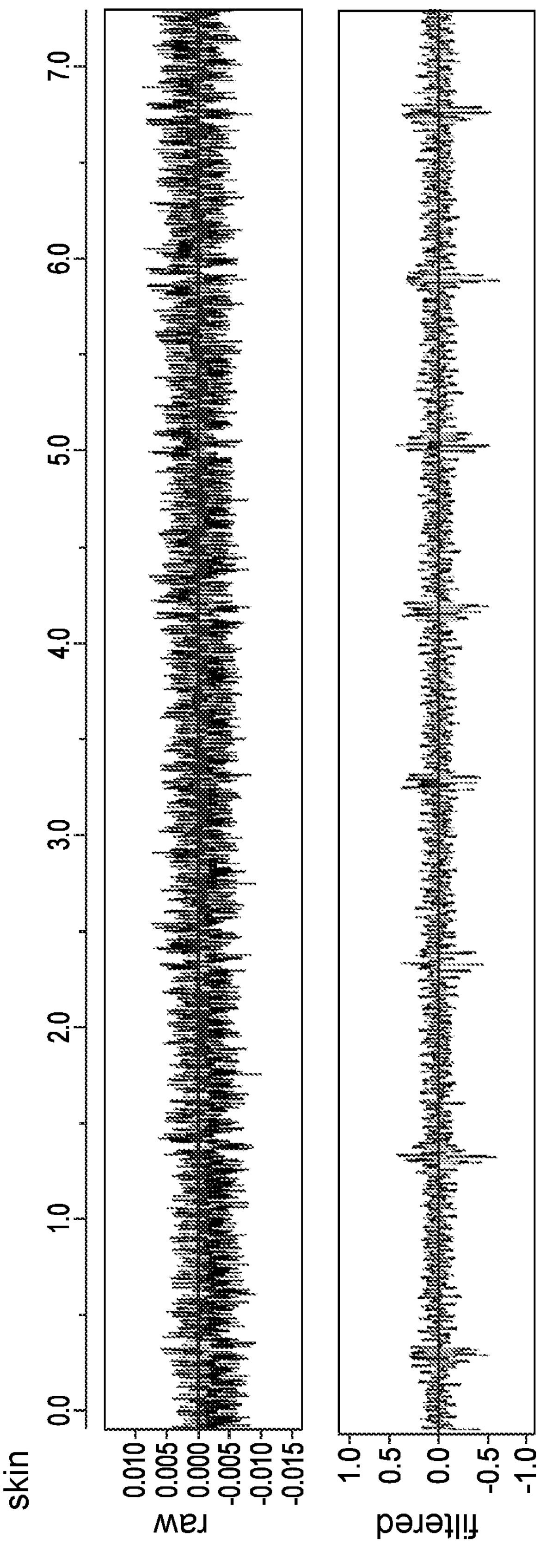
FIG. 9 is an example of raw and filtered signal data collected by a transducer placed against skin in accordance with various embodiments of the present technology.
Figure 10:
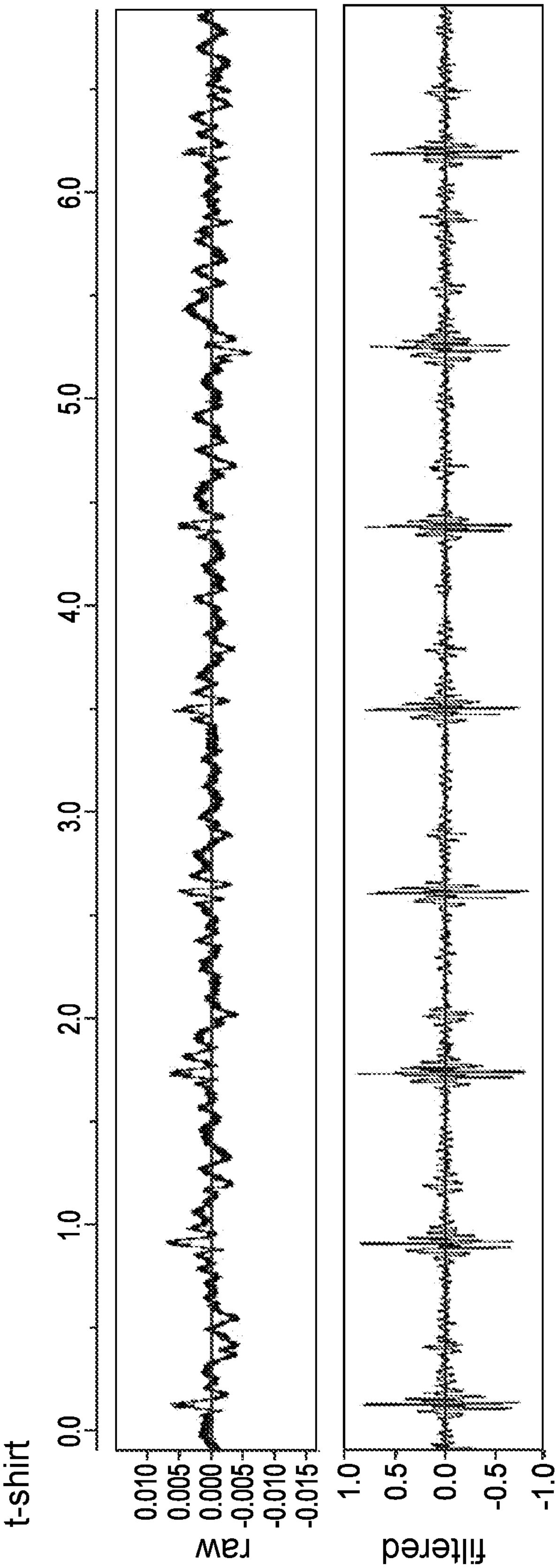
FIG. 10 is an example of raw and filtered signal data collected by a transducer placed against a shirt in accordance with various embodiments of the present technology.
Figure 11:
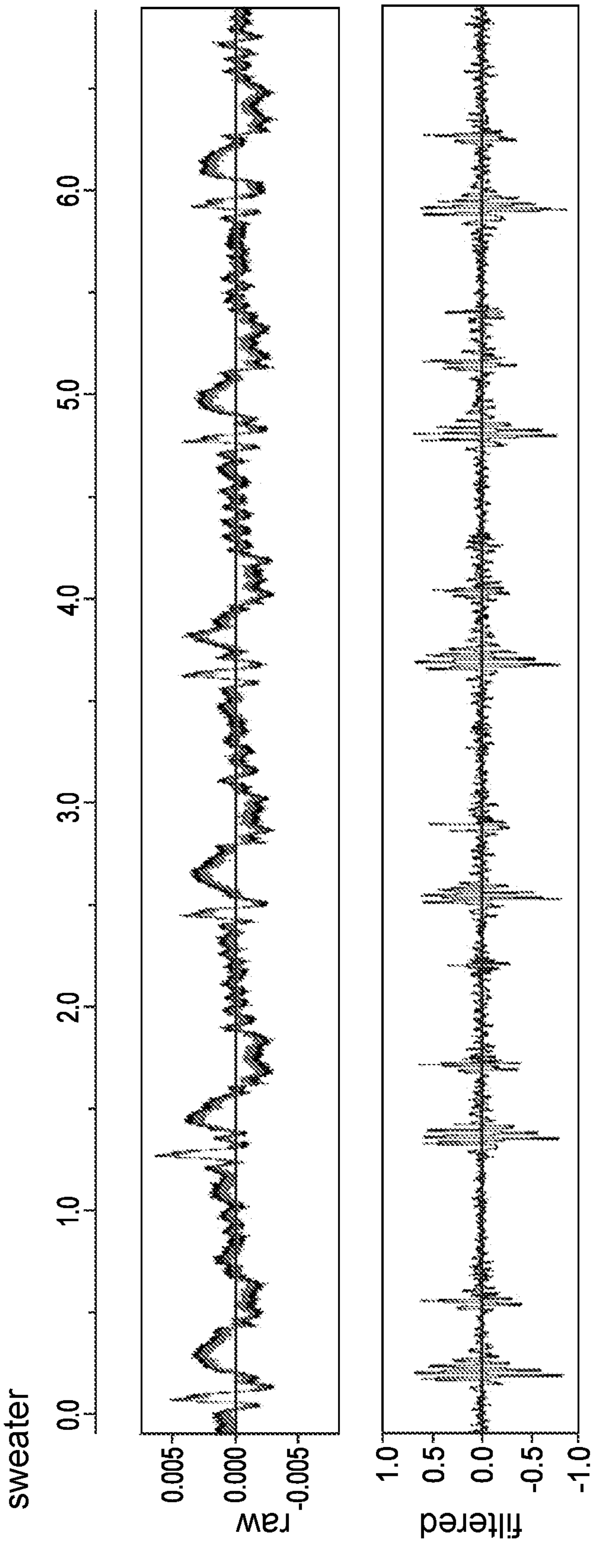
FIG. 11 is an example of raw and filtered signal data collected by a transducer placed against a sweater in accordance with various embodiments of the present technology.

The collected data may be filtered. FIG. 9 illustrates an example of raw and filtered data collected against the skin of a user. FIG. 10 illustrates an example of raw and filtered data collected against a shirt worn by a user. FIG. 11 illustrates an example of raw and filtered data collected against a sweater worn by a user. This indicates that a filtering step can reduce noise associated with the signal.

In yet other experiments, the transducer 100 was held against the carotid artery of a user and could detect a pressure wave generated by blood flow in the carotid artery. The measurement confirmed a heartrate of the user.

Piezoresistive Pressure Sensor

The transducer 100 may be configured to act as a piezoresistive pressure sensor. In this configuration, the piezoelectric layer 130 may be polarized or might not be polarized. The material used for the piezoelectric layer 130 may be blended with carbon. The substrate layer 105 may comprise a diaphragm that is subject to a pressure differential on the opposing faces.

Optical Force Sensor

A transparent electrode layer (e.g. made of PEDOT-PSS) of the transducer 100 may be fabricated in the shape of an optical waveguide and incorporated into an interferometric force sensor.

Combined Sensor

Figure 12:
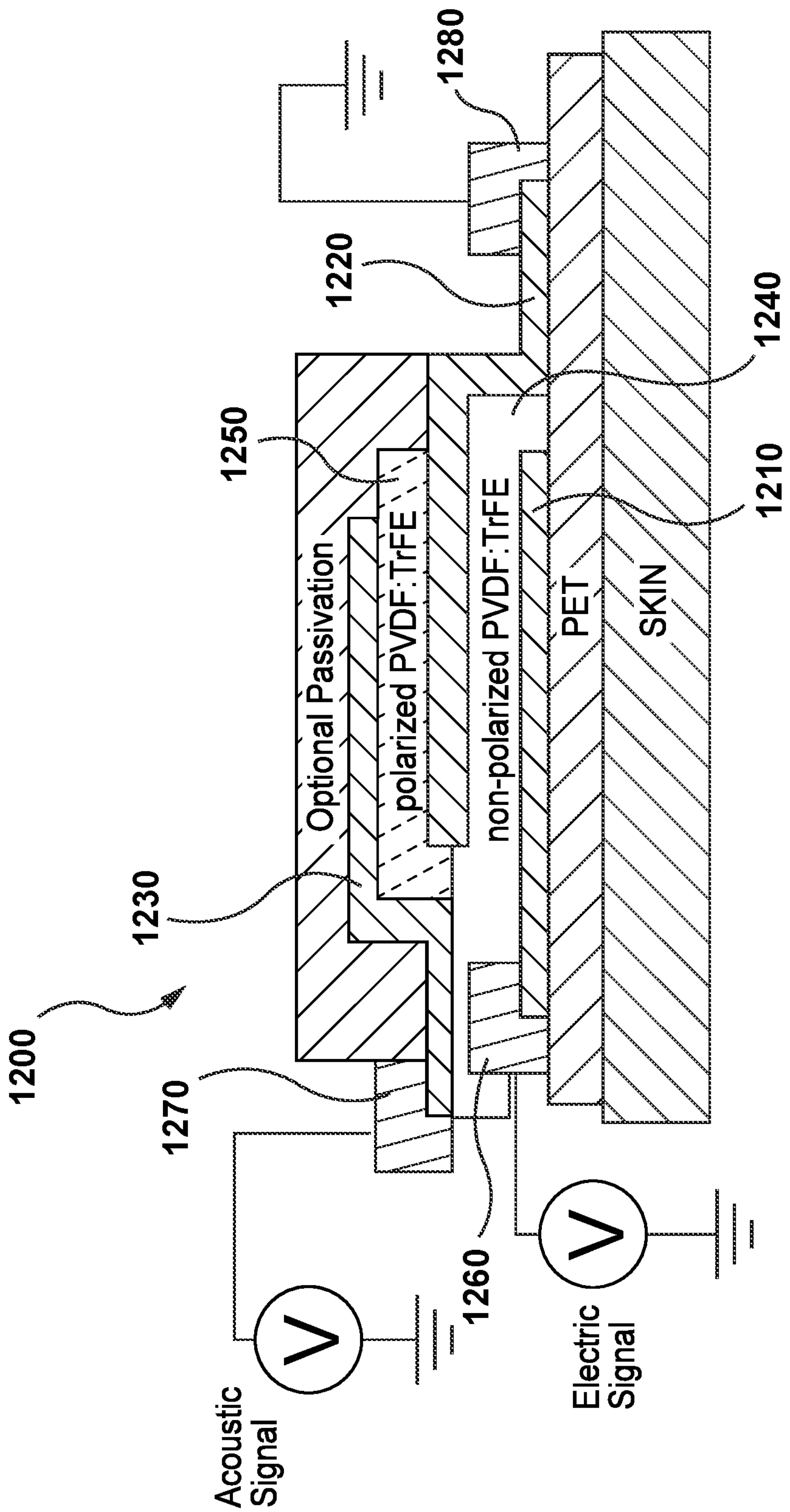
FIG. 12 illustrates a transducer that acts as both an electric potential and an acoustic sensor in accordance with various embodiments of the present technology.

FIG. 12 illustrates a transducer 1200 that acts as both an electric potential and acoustic sensor. The transducer 1200 includes a first electrode layer 1210, second electrode layer 1220, and third electrode layer 1230. The transducer 1200 includes two piezoelectric layers, a non-polarized piezoelectric layer 1240 and a polarized piezoelectric layer 1250.

The first electrode layer 1210 may capture electric potential signals. The first electrode layer 1210 may be the closest electrode layer, of the transducer 1200, to the user's skin in use.

The second electrode layer 1220 may act as a common ground between the first electrode layer 1210 and third electrode layer 1230. The third electrode layer 1230 may collect charges from the polarized piezoelectric layer 1250 when the transducer 1200 is under vibrational stress. The third electrode layer 1230 may be used to measure acoustic data.

The transducer 1200 includes three electrical connectors, a first electrical connector 1260, a second electrical connector 1280, and a third electrical connector 1270. The first electrical connector 1260 may be connected to the first electrode layer 1210, the second electrical connector 1280 may be connected to the second electrode layer 1220, and the third electrical connector 1270 may be connected to the third electrode layer 1230. The first electrical connector 1260 may output a signal corresponding to electric potential. The third electrical connector 1270 may output a signal corresponding to acoustic data. The second electrical connector 1280 may be connected to a ground.

One or more of individual electrode layers, piezoelectric layers and electrical connector layers may correspond to those described previously in terms of composition, thickness and the like.

Combined Sensor—Active Capacitive Sensing

In certain embodiments, the transducer 1200 may function as an active capacitive sensor. Rather than a detected electrical signal flowing from the electrode(s) to the electronics unit, in this configuration an electrical signal may be input to the electrode(s). For example, an active electrical signal may be pushed into the first electrode layer 1210. A second transducer located next to the transducer 1200 or in a same array as the transducer 1200 may act as a capacitive sensor to pick up a response of the target after a signal of active electrode went through the target. The data collected from the active capacitive sensor may be used for: DRL feedback for ECG, skin impedance measurements, active measurement in structural applications, such as water levels, and/or other uses.

Combined Sensor—Electric Potential

In certain embodiments, a multi-layer transducer may be provided which differs from the transducer 1200 in that the second electrode layer is a guard layer, and the third electrode layer is a ground layer. A third piezoelectric layer and a fourth electrode layer may be added above the third electrode layer which may function as an acoustic sensor or an electric potential sensor.

Systems

In certain aspects, there are provided systems incorporating one or more of the transducers described and claimed herein.

In certain embodiments, the system comprises a wearable incorporating one or more of the transducers.

In certain embodiments, the system may comprise a processor of a computer system for receiving the detected signal(s) and further processing. The further processing may include filtering the signal, displaying the signal or the filtered signal, or saving the signal or the filtered signal in a database of the computer system.

The system may include other sensors.

Process for Manufacturing Transducers

Figure 4:
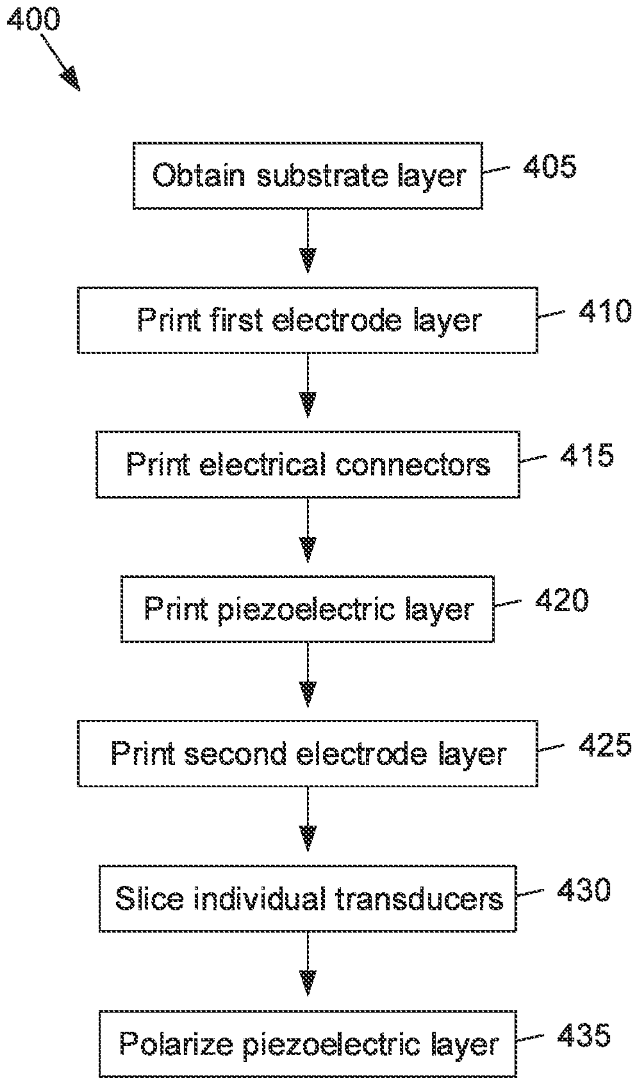
FIG. 4 is a flow diagram of a method for manufacturing transducers in accordance with various embodiments of the present technology.

Referring to FIG. 4, the transducers 100, 210, 220, 230, 710, 720, and/or 1200 may be manufactured using the method 400. It will be appreciated that embodiments of the transducer 100 described herein may also be manufactured in a different manner.

Broadly, the method 400 comprises screen printing and/or ink-jet printing the different layers of the transducer 100. The steps required to manufacture the transducer 100 functional as an electric potential sensor compared to the method steps required to manufacture the transducer 100 functional as an acoustic sensor are the same steps bar one. A sheet containing multiple transducers 100 may be manufactured using the method 400, and then the sheet may be sliced to form the individual transducers 100. In other embodiments, a single transducer 100 may be printed on the sheet.

At step 405 the substrate layer is obtained. The substrate layer may be formed of a substrate composition. The substrate layer 105 may be cleaned, such as in an ultrasonic bath before proceeding to the next step.

At step 410 the first electrode layer 120 is printed. The first electrode layer 120 is formed of an electrode composition. The first electrode layer 120 may be printed on the substrate layer 105. The first electrode layer 120 may be screen printed through a mesh. An annealing process may be applied to the first electrode layer 120 after it is printed on the substrate layer 105. Printing the first electrode layer 120 may comprise printing two or more sub-layers of the first electrode layer 120 to form the first electrode layer 120.

At step 415 the first and second electrical connectors 110 and 115 are printed. The electrical connector 110 and/or 115 may be connectable to an electronics circuit and/or to a ground. The electrical connector 110 is printed so that it contacts the first electrode as well as the substrate in certain embodiments. The electrical connector 150 is printed so that it contacts the second electrode as well as the substrate in certain embodiments.

At step 420 the piezoelectric layer 130 is printed. The piezoelectric layer 130 is formed of a piezoelectric composition. The piezoelectric layer 130 may be printed on the first electrode layer 120. The piezoelectric layer 130 may be screen printed through a mesh. An annealing process may be applied to the piezoelectric layer 130. Printing the first piezoelectric layer 130 may comprise printing two or more sub-layers of the piezoelectric layer 130 to form the piezoelectric layer 130.

The piezoelectric layer 130 may be deposited over a larger area than the first electrode layer 120. The piezoelectric layer 130 may then be trimmed.

At step 425 the second electrode layer 125 is printed. The second electrode layer 125 is formed of the electrode composition. The second electrode layer 125 may be printed on the piezoelectric layer 130. The second electrode layer 125 may be screen printed through a mesh. An annealing process may be applied to the second electrode layer 125. Printing the second electrode layer 125 may comprise printing two or more sub-layers of the second electrode layer 125 to form the second electrode layer 125.

At step 430 the sheet containing all of the printed transducers 100 may be cut around each individual transducer 100 to separate the transducers 100 from each other. Step 430 is optional. In some instances, the individual transducers 100 might not be separated from each other and instead a sensor array may be formed that includes multiple printed transducers 100. As illustrated in FIG. 2, the printed transducer 100 may have multiple layers. A single sheet may have printed transducers 100 with different numbers of layers. For example, a single sheet may include a first printed transducer 210 having two layers and a second printed transducer 230 having four layers.

At step 435 the piezoelectric layer 130 of each printed transducer 100 may be polarized. This step is optional. This step may be performed if the transducers 100 are desired to have acoustic functionality. If electric potential sensor functionality is desired, this step might not be performed. As discussed above, if the piezoelectric layer 130 of a transducer 100 is polarized, then that printed transducer 100 may function as an acoustic sensor. If the PVDF layer of the printed transducer 100 is not polarized, then that transducer 100 may function as an electric potential sensor.

The polarization may comprise applying 100 cycles of +700 to −700 V at 0.5 Hz to polarize the piezoelectric layer 130 of the transducer 100.

In certain embodiments in which a plurality of the printed transducers 100 are formed on a single sheet of material (such as the transducers 710 and 720 of FIG. 7), the polarization step of piezoelectric layers of the same or different printed transducers may be performed at the same time.

In certain embodiments, the steps 410, 415, 420 and 425 may be repeated on an already printed transducer 100 with a first electrode layer, a first piezoelectric layer and a second electrode layer, in order to create a multi-layer printed transducer comprising a first electrode layer, a first piezoelectric layer, a second electrode layer, a second piezoelectric layer, and a third electrode layer (such as the transducer 1200 of FIG. 12). The first and second piezoelectric layers may remain non-polarized, or the method 400 may comprise an additional step of polarizing one or both of the first and second piezoelectric layers.

In some variations, the devices described herein may comprise base primitives created by additive manufacturing methods where a plurality of materials are added layerwise in the z-direction. Some non-limiting examples of the shapes of these primitives are shown in FIGS. 3 and 5.

The additive manufacturing methods may comprise varying the ink types, polymer types, metal types of other material types in the x-, y-, and z-coordinates either through nozzle movement, table movement, or the use of different silk screen or stencil mask changes.

Such techniques of varying the composition of the additive material can provide for the manufacture of so-called 4-D material exhibiting shape memory and auxetic properties that are useful in applications such as, but not limited to, vascular, or other medical stent devices. In some variations, genetic algorithms may be employed to develop personalized primitive-shape memory polymer vascular stents exhibiting auxetic nature.

Key to the shape-shifting auxetic metamaterial technology is the printing paste, which has to be developed individually following models with regard to the layout, powder and impregnated elastomer/electroactive composite containing ferromagnetic microparticles. Sensitive rheologic parameters and intricate process settings allow for the preparation of delicate components with a minimum line width of 10-60 μm and an aspect ratio of more than 100. A supporting powder bed might not be used in hollow structures (canals and cavities) and undercuts are producible without subsequent machining. This provides the opportunity of new revolutionary part designs for many shape-shifting wearable (medical) applications.

Example 1

Following the method 400 described above, in one embodiment, the fully printed transducer was fabricated on a 125-μm thick Melinex ST506 Polyethylene terephthalate (PET) film substrate.

The first electrode layer was made of PEDOT:PSS (Agfa Orgacon EL-P5015) and was formed by screen printing through a mesh polyester 200 cm-1/27 μm using 60 N force and 200 mm/s velocity. The printed layer was then annealed at 120 °C for 20 min; the thickness was approximately 400 nm.

The first and second electrical connectors were printed using Silver ink (Dycotec 3061-S). Screen-printing parameters: mesh polyester 100 cm-1/40 μm, 80 N force, 50 mm/s velocity. Annealing was performed in a standard convection oven at 110 °C, 15 min.

Further, the first piezoelectric layer comprised a 10 μm layer of poly(vinylidene fluoride-co-trifluoroethylene) [P(VDF-TrFE)] (Piezotech ink P FC80/20) which was formed by screen printing using mesh polyester 71 cm-1/55 μm, 100 N, 100 mm/s. This was annealed at 135 °C for 5 min. The printing/annealing step was repeated 4 times to get 10 μm thickness (each step created a 2.5 μm layer). The annealing of the final layer was performed for 20 min at 135 °C The second electrode layer of the transducer was formed with PEDOT:PSS using a screen-printer and annealed at 120 °C for 20 min and 400 nm thickness. This was the same methodology as the printing of the first electrode layer.

Polarization was performed by contact poling, 100 cycles of +700V to −700V and back at 0.5 Hz frequency using an AIXACT TF2000 analyzer.

Screen Printing Process

The first and second electrode layers and the piezoelectric layer were formed by screenprinting. Room temperature was maintained for stable and reliable printing. The clearance between the substrate and mask was 1.2 mm. All screens comprised an aluminum frame with polyester mesh.

Masks were created by the following procedure:

a. 18 μm thick Ulano CDF Vision dual capillary film was laminated on the polyestermesh
b. Print out of desired pattern on clear foil was positioned on top of the screen, then exposed to UV light with a 3000 W mercury lamp (exposure time=900 s)

c. UV light hardens exposed polymer, and the non-hardened polymer is washed away by water.

Example 2. Screen Printing of P(VDF-TrFE)

Device Parameter Optimization: PVDF Thickness Substrate Thickness Device Area/Shape Piezo-Electric Material

TABLE 1

| batch + sample | substrate | PVDF thickness | Polarization | Shape |
|---|---|---|---|---|
| s42-21A | 25-500 μm | 1-10 μm | +/− | Base primitives |
| s42-21B | 25-500 μm | 1-10 + 1-10 μm | +/− | Base primitives |
| s42-21C | 25-500 μm | 1-10 + 1-10 + 1-10 μm | +/− | Base primitives |
| s42-21D | 25-500 μm | 1-10 + 1-10 + 1-10 + 1-10 μm | +/− | Base primitives |
| s42-21E | 25-500 μm | 1-10 μm | +/− | Base primitives |
| s42-21F | 25-500 μm | 1-10 + 1-10 μm | +/− | Base primitives |
| s42-21G | 25-500 μm | 1-10 + 1-10 + 1-10 μm | +/− | Base primitives |
| s42-21H | 25-500 μm | 1-10 + 1-10 + 1-10 + 1-10 μm | +/− | Base primitives |

For the parallel plate capacitive structures, the silver (Ag) paste was used for the first and second electrodes. The viscosity of the paste was in the range of 1-100 Pa·s. The conductive tracks for first electrodes were divided into 2-10 modules of 2×2 to 5×5 array each. The sensing or active area was 1-5×1-5 $mm^2$, connected through 50-100 μm wide printed interconnects. The distance between two adjacent sensors was 1.2-9.6 mm. The 0.5-0.5-5×5 $mm^2$ pads for the readout signals were coupled with printed bottom electrodes.

After first printing step the samples were sintered at 120 °C for an hour. A separate stencil mask with 0.5-0.5-9×9 $mm^2$ opening area, overlapping the bottom electrode was then used for printing of P(VDF-TrFE). Both stencil masks are designed to maintain the overlay registration accuracy. The critical parameters for screen-printing parameters such as squeegee height, pressure on the stencil, speed, snap-off and offset for the screen stage were all monitored to obtain efficient printing. Deposited layers were sintered in vacuum at 140 °C for about 4 hours to completely remove the solvents and enhance recrystallization of P(VDF-TrFE). The top electrodes were then patterned on a separate PET substrate using the stencil mask, which was employed for the lower electrodes. However, the stencil was rotated by 90° with respect to lower electrode to obtain sensors in the row-column fashion as shown in Table 1.

Flexible Sensors, Including Piezo-Resistive, Piezo-Electrical, Capacitive, and Field Effect Transistor-Based Multistable Mechanical Wearable Metamaterials Smart flexible sensing electronics are components crucial in endowing health monitoring systems with the capability of real-time tracking of physiological signals. These signals are closely associated with body conditions, such as heart rate, wrist pulse, body temperature, blood/intraocular pressure and blood/sweat bio-information. Monitoring these physiological signals provides a convenient and non-invasive way for disease diagnoses and/or health assessments. This disclosure describes the novel integration of flexible sensing electronics and fabric/metamaterial mechanical engineering for their use in continuous wearable/attachable health monitoring systems. This disclosure presents an overview of different metamaterials and configurations impregnated with a targeted variety of flexible sensing electronics, including piezo-resistive, piezo-electrical, capacitive, and field effect transistor based devices, provides data-driven design principles, and analyzes physiologic data in light of the working principles in monitoring physiological signals. Described herein are novel approaches and insights on the design of flexible electronic devices and systems for physical and chemical monitoring. Material innovation, sensor design, device fabrication, system integration, and human studies employed toward continuous and non-invasive wearable sensing is described herein.

Continuous Health Monitoring with Flexible Sensing Electronics in Multistable Mechanical Wearable Metamaterials: Principles of Operation The systems, methods, and/or sensors described herein provide for a suite of solutions to continuously monitor physical and structural vital signs as comfortably as possible and be able to detect, prior or current bodily conditions as well predict the likelihood of future bodily conditions in some instances. These wearable medical electronic devices can measure various health indicators such as heart rate, pulse, body temperature, blood glucose, etc. noninvasively in real time by simply attaching them to the human body surface or embedding in clothing. Real-time monitoring of human vital signs can alert users and health care providers to provide early/just-in-time medical care when an individual's physical health indicators are approaching abnormality, thereby enabling early intervention, and avoiding the situation where the opportunity time-window for optimal treatment is missed. Also, flexible electronics may be deformed at will and may detect various signals with high personalized sensitivity, thus can be used in artificial electronic skin, second-skin clothing, motion detection, telemedicine, and/or in-home healthcare. Besides health and disease monitoring, these next-generation flexible and wearable solutions are also aimed at performance enhancement and well-being improvement in order to improve human way-of-life and quality-of-life.

Functional Modules of Multifunctional Flexible Electronics-Based Multistable Mechanical Wearable Metamaterials Integrating multifunctional sensing components into one device, clothing or wearable mechanical solutions is an important advance in continuous functional health state monitoring. Flexible sensing electronics embedded in multistable mechanical wearable metamaterials enable detection of multiple signals such as strain, pressure, temperature, humidity, gas, and so on into a single device to provide more comprehensive human health and environmental information. Sensor fusion, data fusion and time-synchronization of multiple layers of thin electronic films encompassing different sensing functions together is a key and novel differentiator of the structural and physical multifunctional sensors described herein.

Flexible Force Sensors

The various stimuli (biochemical, electro-mechanical, and mechano-acoustic transduction) activity underlying regular physiological activity of human body contain many important health information, for instance, heartbeat rate, muscle movement, respiration rate, gut motility and blood pressure. The force sensor can detect and quantify the integration of these electro-mechanical, and mechano-acoustic transduction forces expressed as tension, pressure, torque, stress, and strain by converting them into electrical signals.

Traditional force sensors may be bulky and heavy because they are mostly based on metal and semi-conductor materials, and they are not applicable to wearable electronics for monitoring vital signs of human body due to their greatly limited portability and flexibility. Compared with traditional force sensors, flexible force sensors using plastic and elastomeric substrates, such as the printed transducers described herein, have a series of advantages, such as modularity, better biocompatibility, stretchability, transparency, wearability, washability, re-usability, conformability and capability of continuous detection. In some variations, the entire garment is essentially an extended biosensor. In still other variations, the biosensor is a two-way transducer that can apply mechanical, electrical, magnetic or optical stimuli to the subject in response to biosensor readings or where otherwise determined to be desirable for treatment and rehabilitation.

Resistive Force Sensors

A resistive sensor converts the change in resistance of sensitive materials caused by an external stimulus into an electrical signal output. The active materials of flexible resistive force sensors are generally elastomer composites formed by incorporating conductive fillers, such as graphene, carbon nanotubes (CNTs), metallic thin film, nanowires, particles, Polyvinylidene Fluoride (PVDF) film sensors, and conductive polymers into elastomers (e.g., PDMS, PU, SEBS). The resistance change of the sensor is mainly caused by the following three factors: (i) changes in the geometry of sensitive elements, (ii) the change of the gap between nanoparticles or nanowires, and (iii) changes in contact resistance between different layers of materials.

Piezoresistive sensors are of interest in wearable devices due to their low power consumption, simple manufacturing processes, and potential wide application. The utilization of substrates with microstructure surface offers an effective way to fabricate highly sensitive piezoresistive force sensors. For example, the impregnation of flexible piezoresistive sensors into fabric/metamaterials by employing micropyramid polydimethylsiloxane (PDMS) array enhances the pressure sensitivity of the sensor. In addition, non-intuitive shape structures like micropyramid substrates can maximize the geometry change of the conductive electrode induced by pressure or stretching, significantly improving the sensitivity while retaining good linear response to pressure.

Capacitive Force Sensors

A capacitor generally consists of a dielectric layer sandwiched by two conductive plates. Capacitive sensors response indicates changes in the external forces through changes in capacitance. When an external force is applied to the sensor to cause deformation, the total volume of air voids in the dielectric layer decreases and the permittivity of air/elastomer hybrid dielectric layer increases, so that the rise in the capacitance value of capacitive sensors caused by two factors: the reduction in the plate spacing and the increase of permittivity.

The formula used to calculate the capacitance is:

$$C = \frac{\varepsilon_0 \varepsilon_r A}{d}$$

where $\varepsilon_0$ is the vacuum permittivity, $\varepsilon_r$ is the relative permittivity of the dielectric, A is the effective overlap area of the two conductive plates, and d is the spacing between the two conductive plates. The sensing ability of capacitive sensors can be significantly enhanced by microstructuring electrodes or dielectric layers. The electrodes of flexile capacitive force sensors usually use carbon nanotubes (CNTs), Ag nanowires, and conductive ionic materials. Compared with resistive sensors, capacitive sensors generally have higher sensitivity and lower detection limits. We have optimized capacitive sensing across low modulus elastic materials including Ecoflex, Styrenic block copolymers based on styrene-ethylene-butylene-styrene (SEBS) and polydimethylsiloxane (PDMS) substrates, in order to improve poor response linearity and reduce susceptibility to parasitic capacitance and fringing capacitance.

Piezoelectric Force Sensors

The piezoelectric effect phenomenon results from the polarization of internal dipoles, leading to potential differences existing between the two opposing surfaces of piezo crystals following mechanical stimuli that partially deforms anisotropic crystalline materials. Due to the unique characteristics of piezoelectric materials, piezoelectric sensors with rapid response time are capable of measuring high-frequency dynamic signals efficiently and can potentially self-power and/or energy harvest.

Flexible Physiological Biochemical Sensors

In order to understand all aspects of human health, various physiological biochemical sensors have been developed for analysis of vital biochemical signs, such as blood glucose and body fluids (sweat, interstitial fluids, saliva, and tears). Flexible biochemical sensors typically adopt chemical methods to detect the composition and amount of a biological substance. The chemical reaction between the sensing material and the target detection substance changes the electrical properties of the sensor, therefore the physiological health information can be obtained by analyzing the electrical parameters of the sensor.

Continuous measurement of glucose is vital to maintain the health and quality of life of diabetics. Commercially available products for glucose detection are performed by invasive lancet approaches that requires sampling the patient's blood, leading to pain to the patient.

Besides glucose monitoring, sweat analysis can be important in facilitating insight into an individual's heath state. For example, sweat glucose is metabolically related to blood glucose and low electrolyte levels in sweat may be a sign of dehydration.

Continuous Health Monitoring with Flexible Sensing Electronics in Multistable Mechanical Wearable Metamaterials: Novel Integrated Manufacturing Methods Auxetic materials are characterized by a negative Poisson's ratio. They have attracted a lot of attention from both the scientific and engineering communities because of a variety of potential applications, such as impact mitigation, indentation resistance and biocompatibility. The design of auxetic materials is usually realized in lattice-based periodic structures. Disordered networks have the potential for the design of tunable isotropic auxetic metamaterials. However, the design of disordered three-dimensional auxetic networks has been challenging due to lack of a universal design principle.

The electro-mechanical and computational strategies described herein allow systematic design and deployment of disordered three-dimensional auxetic networks. The shape-morphing metamaterial designs described herein are engendered by impregnating auxetic materials with physical/structural functional health state driven piezo-technologies to manipulate the auxetic meta material properties. Developed flexible sensing electronics in multistable mechanical wearable metamaterials can shape-adapt to required shape and form with and without direct mechanical contact, and when compressed they undergo contraction in the directions perpendicular to the applied force (i.e., negative Poisson's ratio characteristic). On the contrary, common materials expand in the directions orthogonal to compressive load. Such complex shape-morphing ability enables the development of pliable materials that can transform to soft-firm-to-hard with pliable shape, form and function limbs.

Herein are described "shape-matching" piezo-technology impregnated metamaterials where the geometry of cellular structures comprising auxetic and conventional unit cells is designed so as to achieve pre-defined shapes in response to structural or physical functional health state measures and/or underlying structural/physical form deformation. Finite element computational models may be used to forward-map the space of planar shapes to the space of geometrical designs allowing for entropy, stochastic and random Fourier's series to direct novel unanticipated and learned designs. The validity of the underlying computational models is demonstrated by comparing predictions with experimental observations on specimens fabricated with indirect additive manufacturing. These shape-matching/shape-shifting meta materials may be deployed in wearable (medical) devices for supporting athletic training and rehabilitation, maternal and fetal health, military/space/aeronautics performance enhancement, well-being/office/aging-in place/perennial health monitoring, etc.

"Shape-matching" piezo-technology impregnated metamaterials may be manufactured on a 3-D printing platform that can enable both the modeling and design of complex magnetically actuated devices. The approach utilizes a 3-D printing platform fitted with an electromagnet nozzle and 3-D printable ink infused with electroactive polymers (EAPs), magnetic particles, etc. The EAP and magnetic ink is model optimized to strengthen soft and transformable functionality, and new on-demand flexible material systems for integration wearable device systems. Piezo-technology impregnated auxetic metamaterials enable control of the magnetic orientation of 3-D printed shape-matching wearable devices so that they are able to rapidly change into new intricate formations or move about as various sections respond to sensed physical/structural functional health state input.

The approach is based on simultaneous 3-D metamaterial printing with direct inkjet printing or silk printing of an elastomer/electroactive composite containing ferromagnetic microparticles and the application of a magnetic field to the dispensing nozzle while printing. The technique reorients particles along the applied field to impart patterned magnetic polarity to printed filaments. EAP and ferromagnetic metamaterial archetype domains are programmed in complex 3-D-printed soft materials to enable a set of previously inaccessible modes of material transformation.

The 3-D shape-modifying auxetic metamaterials screen printing technology described herein is based in part on the well-established 2-D screen printing methods. In an adapted process cycle it is possible to print impregnated elastomer/electroactive composite containing ferromagnetic microparticles and auxetic multilayers of the desired layout on top of each other to generate 3-D structures. Layer by layer a binder stabilized impregnated metamaterial part is built which has to be heat treated to full density subsequent to the printing process.

By programming complex information of structure, domain, and magnetic field, one can print intelligent metamaterials for performance enhancement, health/well-being promotion, disease prevention, treatment, rehabilitation, etc. The actuation speed and power density of the printed soft materials with programmed EAP and ferromagnetic domains may be greater, such as by orders of magnitude, than existing 3-D-printed active materials. Functions demonstrated from these complex shape changes include reconfigurable soft electronics, mechanical metamaterial that can fit tighter or loosen or deliver pharmaceuticals in response to sensed functional health state input, or recognized activity.

Electroactive Polymers

There are different electroactive polymers (EAPs), namely, Nylon-11, polylactide and aniline pentamer copolymer, poly(lactic-co-glycolic acid) (PLGA), and poly(vinylidene fluoride) (PVDF) and its copolymers with trifluoroethylene (TrFE). Amongst them, PVDF and PDVF-TrFE exhibit the best electroactive properties, such as piezo-, pyro- and ferro-electricity. Polyvinylidene fluoride-trifluoroethylene (PVDF-TrFE), is a copolymer that exhibits piezo-, pyro- and ferro-electric properties. The piezoelectric materials used for structural and physical health monitoring applications range from ceramics such as lead zirconate titanate (PZT) and polymers such as Polyvinylidene fluoride (PVDF) and respective copolymers. Generally, the ceramics such as PZT have higher piezo/pyroelectric constants and higher sensitivity than polymers. PVDF and its copolymers enjoy the advantage of mechanical flexibility and easy processing through solution deposition. For this reason, we have investigated PVDF and its copolymer such as P(VDF-TrFE) for large area sensing thoroughly. PVDF and its copolymer such P(VDF-TrFE) also exhibit stable piezo, pyro and ferroelectric properties. Other attractive features of P(VDF-TrFE) are good pressure sensitivity, wide frequency response, cost effectiveness, ease of fabrication and light weight. Piezoelectric materials are unique as they allow us to measure dynamic touch or contact events and also enable multiple uses as sensors, actuators and energy harvesters. Contact parameters such as temperature, proximity and pressure can be measured using sensors based on diverse transduction methods, including capacitive, piezoresistive and piezoelectric etc. Piezoelectric and piezoresistive tactile sensors can be printed on large areas and bendable substrates, which may be needed for conformal covering of 3D surfaces such as second skin use cases.

Inkjet Printing

The inkjet printing technique, in comparison to other direct write techniques, such as dip-pen nano-lithography (DPN), nanofountain pen (NFP), laser-induced forward transfer (LIFT) etc, is a contact free additive printing technique for positioning droplets of liquid material with high precision onto a substrate at room temperature in ambient conditions and involves the use of fewer hazardous chemicals. Moreover, inkjet printing is flexible, versatile and can be set up with relatively low effort, and allows the large scale printing of a wide range of materials. Therefore, printing processes are an efficient way to produce different types of electronic components, such as printed circuits, displays (OLEDs), RFID antennas, batteries and sensors, at low cost. Among the two different methods of drop generation, namely, continuous inkjet (CIJ) and drop-on-demand (DoD), the DoD inkjet printing mode does not require any fluid recirculation, provides higher resolution and generates individual drops whenever needed. The DoD system is more economical, produces less material waste than the CIJ system, and therefore is often used for microelectronics manufacturing.

The drop-on-demand (DoD) inkjet printing technique for microelectronics allows the use of flexible substrate, organic and inorganic materials, and low-cost volume fabrication. The operating principle of the DoD mode inkjet printing system can be described as a sudden change in volume caused by the voltage applied to the piezo-electric actuator, which produces the pressure waves that propagate throughout the capillary. The fluid is pushed outwards when the positive pressure wave approaches the nozzle. Eventually, the ejection of a droplet takes place when the amount of kinetic energy transferred outwards is larger than the surface energy needed to form a droplet. The velocity of the droplet depends on the amount of kinetic energy transferred. To overcome the decelerating action of ambient air, the initial velocity of a droplet has to be several meters per second.

In the case of inkjet printing, droplets are ejected through nozzles with diameters of a few tens of micrometers at velocities typically higher than 10 m s−1. As a result, polymer solutions undergo a high elongational deformation, which causes stretching and orientation of polymer macromolecules to a greater extent than ordinary shear flow. High molecular weight polymer solutions are known to develop a strong resistance to elongational deformations which results in an increase of elongational viscosity. This is overcome by further decreasing of the shear viscosity induced by shear-thinning behavior in the case of rapid elongational flows. This high resistance to extensional flow occurs when the macromolecular chains undergo a transition from an initial coiled state to a stretched state, which results in the development of a marked restoring force. This force is essentially of an entropic nature: an imposed elongation reduces the number of possible configurations and therefore the entropy.

During the development of the flexible sensing electronics described herein in multistable mechanical wearable metamaterials, inkjet-printed films using high molecular weight PVDF-TrFE were developed and characterized to optimize their morphology and crystallinity. Modified waveform and very low jetting frequency methods were developed to accommodate relaxation time of the polymeric ink during jetting. In certain variations screen printing may be preferred.

Screen Printing

The simple processing steps, fast production of sensors, and uniform deposition of materials over large areas make screen-printing an attractive additive manufacturing method. Screen-printing is an established mature technology with stable processing conditions. Further, the materials for optimum physical and electrical characteristics have already been developed over the years. It has been used to realize multilayer high-density flexible electronic circuits with embedded passive and optical devices, large area humidity and temperature sensors. Screen printing is attractive for capacitive structures of P(VDF-TrFE), as there are no moving tools and parts, which means there are lesser issues to deal with related to the sensor design, fabrication, interconnects and packaging. The major research on employing screen-printing for piezosensors has been about patterning of electrodes and sensing area on commercially available PET sheets.

Due to the sophisticated printing of paste next to and onto already printed 3-D structures the screen has to be changed in a defined sequence and aligned perfectly to avoid flaws. Experiments proved the feasibility of this concept: 3D test patterns can be printed with a linewidth of 50-250 μm and printed samples of copper and ceramic were sintered without cracks to a density of more than 70-92%.

Since the 3-D and 2-D printing and burning steps are executed consecutively, it is possible to apply an adapted heat treatment to meet both materials requirements. For this reason 3-D screen printing is the most promising additive manufacturing method today to be able to fabricate functional components consisting of two or more materials in one step. The potential fields of application are literally endless and include electromagnetic energy converters such as electric motors, and generators, electromagnetic switches, integrated sensors, RFIDs, relays and generally, other electronic or electromagnetic devices.

The two table setup allows high build rates up to 160 $cm^3$/h, which makes it faster than many other 3-D-printing technologies. For example, selective laser melting (SLM) may be used with about 40-80 $cm^3$/h. The developed 3-D screen and stencil printing method constitutes a first step towards the mass printing usage of this approach. Advanced setups with several printing stations and tables will be able to manufacture more complex parts en masse.

Piezoelectric materials commonly used in flexible sensors include P(VDF-TrFE), ZnO, PbTiO3, PZT, and/or any other suitable piezoelectric materials. In some variations, Polyvinylidene fluoride-trifluoroethylene (PVDF-TrFE) is preferred for mechanical and acoustic sensors, transducers, actuators, energy harvesting and nonvolatile memory applications. The PVDF-TrFE copolymer exhibits some advantages over the pure PVDF polymer, as the copolymer typically shows much higher crystallinity and a larger piezoelectric response. The addition of trifluoroethylene (TrFE) introduces more fluorine atoms into the polymer chain and prevents the molecular chains from accommodating a 'trans-gauche-trans-gauche' conformation due to the steric hindrance imparted by the bulky fluorine atoms. As a result, the copolymer is normally oriented directly in the extended 'all-trans' conformation even without the application of any physical methods, such as stretching, annealing or quenching.

A number of fabrication technologies may be used for P(VDF-TrFE) based sensors. These include spin coating, thermally drawn functional fibers, micro-machined mold transfer, single and multiplayer inkjet printers and electrospinning processes. The issues with most frequently used techniques such as spin coating and inkjet printing are the poor processing speed and overlay registration accuracy, especially in multilayer structures. The spin coating route for patterning of P(VDF-TrFE) also requires additional photolithography steps, which add to the cost of fabrication. The proposed 3-D/2-D printed electronics direct write techniques solves these problems.

Thus, the methods and/or systems described herein can provide non-invasive as well as invasive devices.

Noninvasive, flexible electronics, wearables include:

1. Electronic skin patches to enable continuous monitoring of medical/wellness/fitness parameters such as heart rate, temperature, and wound pH,
2. Integrated electronics, including capacitive sensors for detecting oil pipe failure, monitoring HVAC performance efficiency, water leaks, rotating parts resilience, imprinting, transparent antennas printed onto glass, and/or any other suitable substrate, and 3. Sticker electronics, in which flexible stickers containing antenna, sensors and mounted integrated circuits to enable remote monitoring of packages and industrial equipment.

Invasive, flexible electronics, wearables include:

1. Surgical instrumentation. Applying an auxetic structure to these devices provides stability and high-performance. Auxetic foam and honeycomb filters help clean the fouled filters, adjust pore size and shape, and compensate for the effects of pressure build-up due to fouling better than non-auxetic filters, since stretching the auxetic filters improves the performance by opening pores in both directions.
2. Auxetics are widely utilized in the manufacture of angioplasty stents, annuloplasty rings, and esophageal stents, where they are used as dilators. Impregnating stents with piezo technology enables them to change shape as required. Most importantly the stents can also behave as an antenna and communicate with the outside world once implanted. 4-D Primitive-shape stents are expected to exhibit up to 3-to-7 times better energy absorption capability than conventional 2-D stents.
3. Orthopedic bone plates. Re-entrant primitive shape honeycomb incorporated bone plates are expected to exhibit better stress-shielding and intra-operative bending than their conventional counterparts. Auxetic structures can also improve the bone screw fixation.
4. Potential use of microporous hollow auxetic structures as mechanical lungs, liver, and gut is also possible.
5. Auxetic structures in medical bandages is also possible. The swelling of the wound and force on the bandage results in the controlled release of the wound-healing agent.

Sensors and Actuators

The methods and/or systems described herein provide the next generation of structural/physical sensors by integrating auxetic materials and biomimetic principles.

1. Auxetic mechanical metamaterials with their negative Poisson's ratio are used in stretchable strain sensors provide great sensitivity (10-to-50-fold improvement over conventional sensors).
2. Piezoresistive sensor with a re-entrant auxetic structure and auxetic microfiber sheets (AMSs), auxetic solid sheets (ASSs), microfiber sheets (MSs), and solid sheets (SSs) can be fabricated for the design of stretchable force sensors to stretch up to 50-350%.

A tunable Poisson's ratio is an important property of the piezo technology substrates. For a $v<=-0.1$, the auxetic force sensor can exhibit piezoresistive ability that is 50-350% better than conventional sensors. For example, an auxetic structure made up of silicon rubber and chopped carbon fiber and manufactured using a 3D printing technique, fabricated an auxetic sensor is highly sensitive in low strain. The sensitivity to low strain makes this sensor biaxially stable, and a high-performance conductor. Owing to the negative Poisson's ratio, the sensor matches perfectly the deformation of the skin, is durable, and provides stable performance in varied environments and is useful in applications such as measurement of vibrations of the earth, rotor strain and body pulse.

Vibrome Shell

Shape-memory properties coupled with auxetic structures can been used to manufacture smart flexible sensors, antennas, and some deployable structures that need no external actuation. Furthermore, re-entrant auxetic structures and can move and guide, needles for example, due to the combined effects of pneumatics, inchworm kinematics and multimaterial additive manufacturing. Computational methods may be used which leverage domain adaptive ML/AI learning algorithms in combination with discrete element simulations to design mechanical actuators by training a deep neural network. Auxetic materials can also be used in the design and manufacture of hydrophones, because their low bulk modulus makes them more sensitive to pressure changes. Other uses/implementations include:

1. Auxetic porous membranes grafted by polymers in valves and sensors.
2. Incorporating magnetic components into auxetic structures for use with external magnetic-fields to tune their macroscopic properties, e.g., Left-and right-handed cylinder-based linear actuators using the handed shearing auxetic structures to create 2-Degree-of-freedom and 4-degree-of-freedom actuators.
3. Soft cylindrical actuators which exhibit reversible flexural and twisting motion by taking advantage of the primitive shape void-patterned cylindrical shells that exhibit auxetic behavior.
4. Auxetic re-entrant structure implemented as a 4D primitive tube-like bending actuator where a difference in pressure between the internal and external surfaces of the tube generates circumferential actuation.
5. Auxetic polyurethane foam buckled structure with conductive fabric can be used in self-powered strain sensors, built to sense body movements, and to enhance energy harvesting from ambient vibration.

2nd Skin Clothing and Apparel

In order to apply auxetic materials to next generation clothing and apparel, it is necessary to provide properties, such as comfortability, high energy absorption, high volume change, accurate and reproducible data generation and wear resistance.

1. Auxetic textile materials from 3/4D-primitive shape auxetic yarn are used to develop bullet-proof/knife-proof/blast-proof/tear-proof function by opening up when the pressure wave comes, and in the process, capturing the glass pieces and/or shrapnel. Bullet proof vests can be made out of auxetic materials, which upon impact will become thicker, rather than becoming thinner.
2. The synclastic nature of auxetic materials can be utilized in the manufacture of protective equipment for the elbow and knee joints, which are especially necessary for adventure sports.

Apart from the above, the auxetic materials impregnated with piezo 'shape-shifting' technologies have applications in several other vital areas, such as robotics, agriculture, for the controlled delivery of seeds and fertilizers; paints and dyes, where auxetic material-based paints could completely eliminate the formation of scratches; and in combination with other materials they could also be used for waterproofing by, for example, forming on-command ultrahydrophobic surfaces.

We claim:

1. A transducer comprising a substrate layer, a first electrode layer on the substrate layer, a first piezoelectric layer on the first electrode layer, a second electrode layer on the first piezoelectric layer, a first electrical connector connected to the first electrode layer and a second electrical connector connected to the second electrode layer, one or both of the first electrical connector and the second electrical connector being connectable to an electronics circuit or to a ground.

2. The transducer of claim 1, wherein the transducer functions as an electric potential sensor when the first piezoelectric layer is not polarized and functions as an acoustic sensor when the first piezoelectric layer is polarized.

3. The transducer of claim 2, wherein the first piezoelectric layer is not polarized and wherein one of the first electrical connector and the second electrical connector is connected to an electronics circuit, and the other of the first electrical connector and the second electrical connector is floating, connected to ground, or connected to a shield.

4. The transducer of claim 2, wherein the first piezoelectric layer is polarized and wherein one of the first electrical connector and the second electrical connector is connected to an electronics circuit, and the other of the first electrical connector and the second electrical connector is floating, connected to ground, or connected to a shield.

5. The transducer of claim 1, wherein the substrate layer is flexible.

6. The transducer of claim 5, wherein the substrate layer comprises polyethylene terephthalate (PET).

7. The transducer of claim 1, further comprising an electronics circuit connected to one or both of the first electrical connector and the second electrical connector, and wherein the electronics circuit includes a voltage amplifier, charge amplifier or current amplifier.

8. The transducer of claim 7, further comprising a processor connected to the electronics circuit for receiving signals detected by the transducer.

9. The transducer of claim 1, wherein the transducer has a circumference which is quadrilateral or circular and a surface area of about 70 to about 1500 $mm^2$.

10. The transducer of claim 1, wherein the transducer was formed by printing, sequentially, the first electrode layer on the substrate layer, the first piezoelectric layer on the first electrode layer, the second electrode layer on the first piezoelectric layer.

11. The transducer of claim 1, further comprising a second piezoelectric layer on top of the second electrode layer and a third electrode layer on top of the second piezoelectric layer.

12. The transducer of claim 11, wherein one of the first piezoelectric layer and the second piezoelectric layer is polarized and the other of the first piezoelectric layer and the second piezoelectric layer is not polarized.

13. A method of making a transducer, the method comprising:

obtaining a substrate layer having a substrate composition;

forming a first electrode layer, having an electrode composition, on the substrate layer;

forming a first piezoelectric layer, having a piezoelectric composition, on the first electrode layer;

forming a second electrode layer, having an electrode composition, on the first piezoelectric layer; and forming one or both of a first electrical connector connected with the first electrode layer and a second electrical connector connected with the second electrode layer, wherein one or both of the first electrical connector and the second electrical connector are printed after the first electrode layer and before the first piezoelectric layer.

14. The method of claim 13, wherein forming the first electrode layer comprises printing the electrode composition followed by annealing.

15. The method of claim 13, wherein forming the first piezoelectric layer comprises printing the piezoelectric composition followed by annealing.

16. The method of claim 13, wherein forming the second electrode layer comprises printing the electrode composition followed by annealing.

17. The method of claim 13, further comprising forming a plurality of the transducers wherein the plurality of transducers have a common substrate layer.

18. The method of claim 17, wherein at least two transducers of the plurality of transducers have a first electrode layer or a second electrode layer that share a ground connection.

19. The method of claim 13, further comprising forming a plurality of the transducers on a sheet.

* * * * *